United States Patent [19]
Mondry

[11] Patent Number: 5,682,877
[45] Date of Patent: Nov. 4, 1997

[54] SYSTEM AND METHOD FOR AUTOMATICALLY MAINTAINING A BLOOD OXYGEN SATURATION LEVEL

[76] Inventor: Adolph J. Mondry, 46340 Concord Dr., Plymouth, Mich. 48170

[21] Appl. No.: 228,092

[22] Filed: Apr. 15, 1994

Related U.S. Application Data

[63] Continuation-in-part of Ser. No. 982,389, Nov. 25, 1992, Pat. No. 5,315,990, which is a continuation-in-part of Ser. No. 814,481, Dec. 30, 1991, abandoned.

[51] Int. Cl.[6] .......... A61M 16/00; A62B 7/00; F16K 31/02; A61B 5/00
[52] U.S. Cl. .......... 128/204.23; 128/204.22; 128/632
[58] Field of Search .......... 128/204.18, 204.21, 128/204.23, 204.26, 205.24, 205.23, 716–719, 632

[56] References Cited

U.S. PATENT DOCUMENTS

| | | | |
|---|---|---|---|
| 3,734,091 | 5/1973 | Taplin | 128/716 |
| 4,121,578 | 10/1978 | Torzala | 128/204.23 |
| 4,326,513 | 4/1982 | Schulz et al. | 128/203.14 |
| 4,612,928 | 9/1986 | Tiep et al. | 128/204.23 |
| 4,665,911 | 5/1987 | Williams et al. | 128/204.21 |
| 4,671,297 | 6/1987 | Schulze, Jr. | 128/716 |
| 4,932,402 | 6/1990 | Snook et al. | 128/204.23 |
| 4,972,842 | 11/1990 | Korten et al. | 128/716 |
| 4,986,268 | 1/1991 | Tehrani | 128/204.22 |
| 5,103,814 | 4/1992 | Maher | 128/204.18 |
| 5,315,990 | 5/1994 | Mondry | 128/205.11 |
| 5,365,922 | 11/1994 | Raemer | 128/204.23 |
| 5,388,575 | 2/1995 | Taube | 128/204.23 |

OTHER PUBLICATIONS

"Closed–loop Control of Sao$_2$ in the Neonate", by Paul E. Morozoff, Ron W. Evans From Biomedical Instrumentation & Technology, Mar./Apr. 1992; 26:117–123.

"A Clinical Guide to Cardiopulmonary Medicine", Cress et al., Puritan–Bennett Corporation, Rec'd in PTO 1989, Entire Book 128/200.24.

*Primary Examiner*—Kimberly L. Asher
*Attorney, Agent, or Firm*—Brooks & Kushman P.C.

[57] ABSTRACT

A system and method for automatically selecting an appropriate oxygen dose to maintain a desired blood oxygen saturation level is disclosed. The system and method are particularly suited for use with ambulatory patients having chronic obstructive lung disease or other patients requiring oxygenation or ventilation. In one embodiment, the method includes delivering a first oxygen dose to the patient while repeatedly sequencing through available sequential oxygen doses at predetermined time intervals until the current blood oxygen saturation level of the patient attains the desired blood oxygen saturation level. The method then continues with delivering the selected oxygen dose to the patient so as to maintain the desired blood oxygen saturation level.

12 Claims, 26 Drawing Sheets

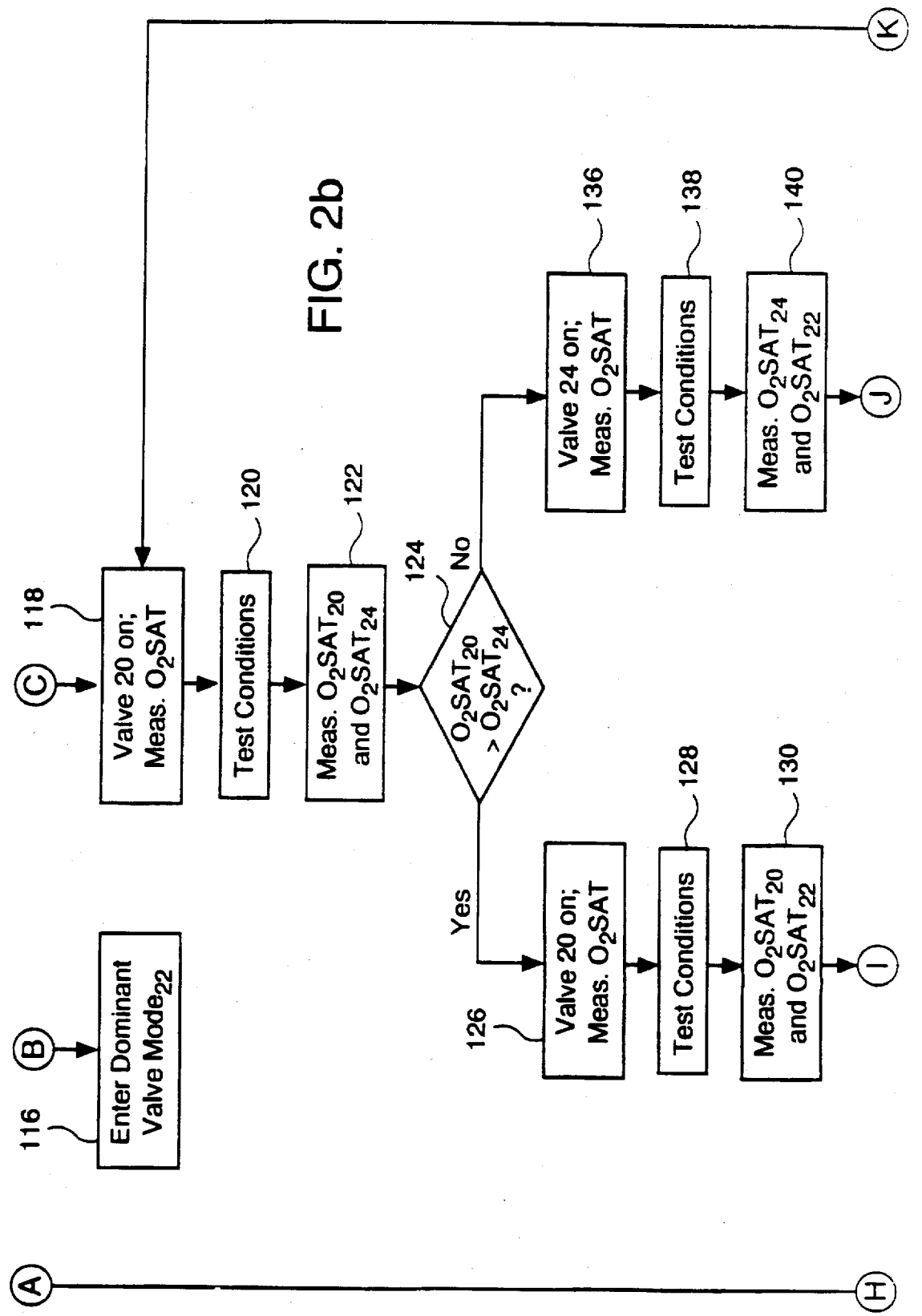

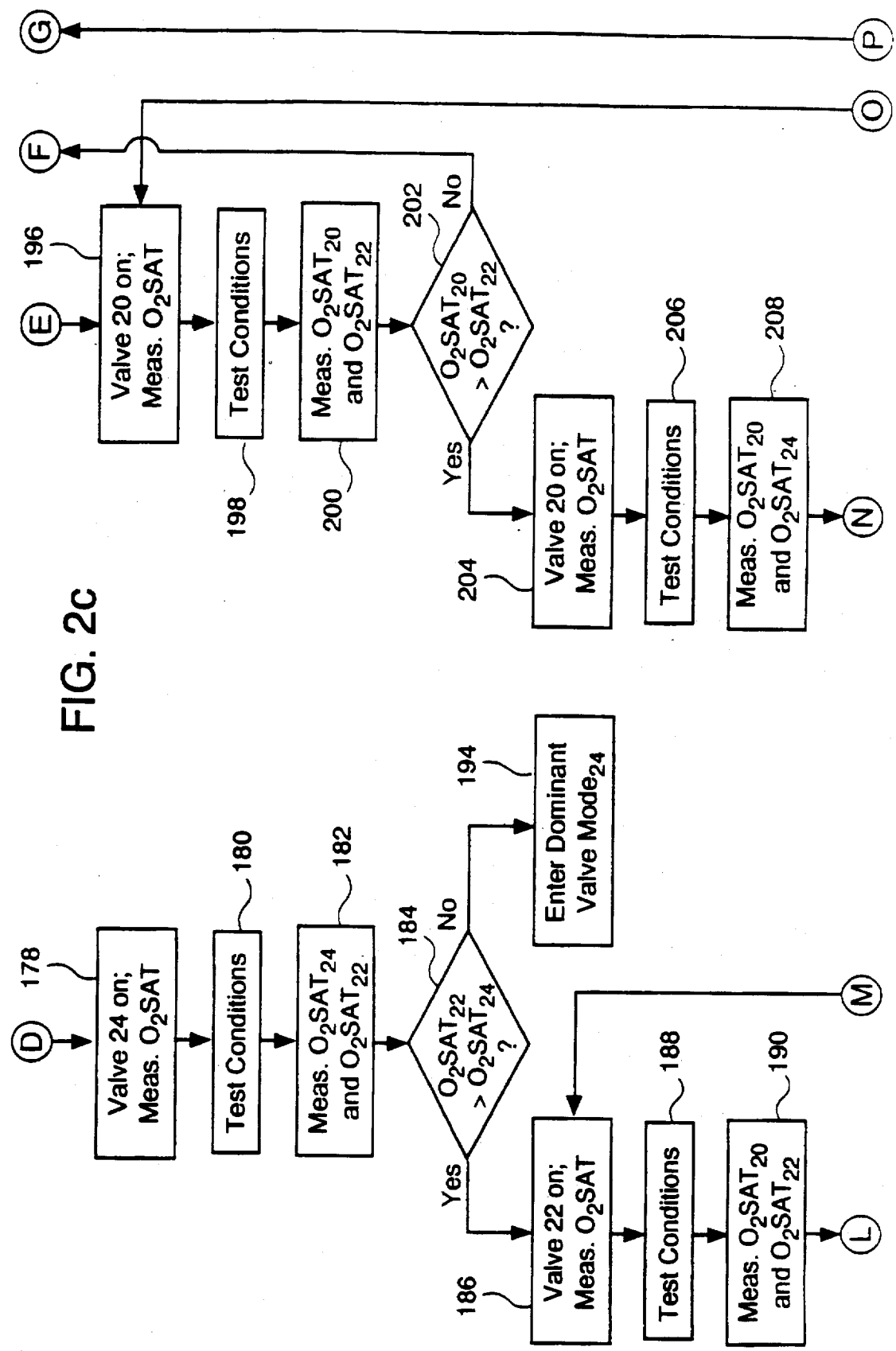

TEST CONDITIONS 102, 110, 120, 128, 138,
146, 156, 162, 172, 180,
188, 198, 204, 216

SYSTEM AND METHOD FOR AUTOMATICALLY MAINTAINING A BLOOD OXYGEN SATURATION LEVEL

CROSS REFERENCE TO RELATED APPLICATIONS

This application is a continuation-in-part of U.S. patent application Ser. No. 07/982,389, filed Nov. 25, 1992, now U.S. Pat. No. 5,315,990, and titled "Method for Delivering Incremental Doses of Oxygen for Maximizing Blood Oxygen Saturation Levels", which is a continuation-in-part of U.S. patent application Ser. No. 07/814,481, filed Dec. 30, 1991, and titled "Oxydosimeter", now abandoned, the disclosures of which are hereby expressly incorporated by reference in their entirety.

TECHNICAL FIELD

The present invention relates to an oxydosimeter for affecting the blood oxygen saturation $SaO_2$ in patients using oxygenators and ventilators.

BACKGROUND ART

Oxygenators and ventilators treat patients who need supplemental oxygenation or who are unable to breathe independently. Recently, a variety of oxygenators and ventilators have been proposed. However, these devices permit significant variation in the blood oxygen saturation level of the patient. The oxygen saturation level $SaO_2$ of a healthy patient breathing room air exhibits little variation.

Significant variation of the oxygen saturation level of a patient may lead to a number of adverse consequences. For example, poor weight maintenance or gain (due to negative nitrogen balance), increased frequency of apnea and poor development in neonates, increased frequency of oxygenation advancement, difficulty in weaning from a ventilator, poor mentation, and decreased survival rates may result. Thus, it is desirable to provide a device which minimizes the variance of the oxygen saturation level $SaO_2$.

In ambulatory patients with chronic obstructive pulmonary disease (COPD), increasing blood oxygen saturation $SaO_2$ may prolong life. Maintaining an increased oxygen saturation level may prolong life even further. Thus, it is desirable to provide a device which maximizes oxygen saturation level, and maintains this increased level $SaO_2$ for patients with COPD.

DISCLOSURE OF THE INVENTION

It is an object of the present invention to provide a method and apparatus for maintaining an increased blood oxygen saturation level $SaO_2$ in patients using oxygenators or ventilators so as to minimize variance of the blood oxygen saturation level $SaO_2$.

Another object of the present invention is to provide a method and apparatus for minimizing the variance of the partial pressure of oxygen $PaO_2$ so as to maintain constant blood partial pressure of oxygen $PaO_2$ levels in patients using oxygenators or ventilators.

It is a further object of the present invention to provide a method and apparatus for maximizing the blood oxygen saturation level $SaO_2$ in ambulatory adult patients with chronic obstructive pulmonary disease.

In carrying out the above objects and other objects and features of the present invention, a method is provided for maintaining a desired blood oxygen saturation level $SaO_2$ in a patient utilizing an oxydosimeter for delivering an oxygen dose selected from one of a plurality of sequential oxygen doses between a first oxygen dose and a second oxygen dose. The method includes delivering the second oxygen dose to the patient while repeatedly sequencing through the plurality of sequential oxygen doses beginning with the first oxygen dose and proceeding to an adjacent oxygen dose in the sequence after a predetermined time interval has elapsed. The second oxygen dose is delivered until the current blood oxygen saturation level $SaO_2$ of the patient attains the desired blood oxygen saturation level $SaO_2$, at which point a corresponding oxygen dose is selected from the plurality of sequential oxygen doses. The method also includes delivering the selected oxygen dose to the patient so as to maintain the desired blood oxygen saturation level $SaO_2$.

A system is also provided for carrying out the method of the present invention.

The advantages accruing to the present invention are numerous. For example, oxydosimeters of the present invention, used in ambulatory patients with COPD, deliver incremental metered doses of oxygen. Typically, this results in increased patient comfort, decreased right-sided heart strain and failure, and increased life span.

Additionally, the oxydosimeters of the present invention, for use with ambulatory patients with COPD, are portable. The portability allows treatment of patients outside the traditional hospital setting. A still further advantage of the present invention is a reduction in patient oxygen consumption. Since the system operates without the need for continual manual adjustment, patient care is reduced with an accompanying reduction in medical costs.

The above objects and other objects, features, and advantages of the present invention will be readily appreciated by one of ordinary skill in the art from the following detailed description of the best mode for carrying out the invention, when taken in connection with the accompanying drawings.

BRIEF DESCRIPTION OF THE DRAWINGS

FIGS. 2a–2f are flow charts detailing the oxygenation strategy of the present invention for use with the adult COPD oxydosimeter shown in FIG. 1;

BEST MODE(S) FOR CARRYING OUT THE INVENTION

Adult COPD Oxydosimeter

Figure 1:
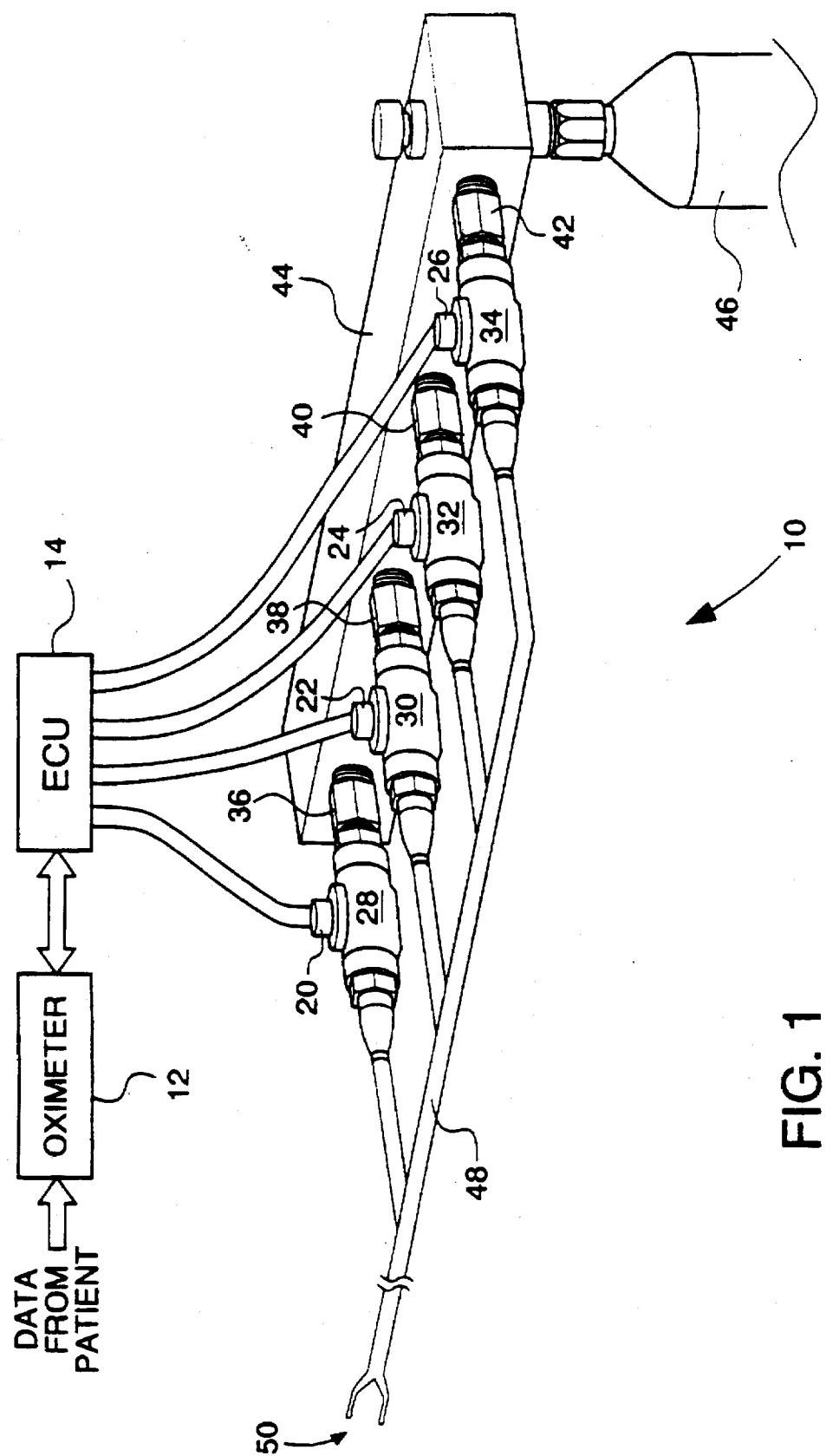
FIG. 1 is a perspective view of a first oxydosimeter embodiment of the present invention, for use as an adult COPD oxydosimeter.

Referring now to FIG. 1, a preferred embodiment of the oxydosimeter system of the present invention, for use as an adult COPD oxydosimeter, is shown generally by reference numeral 10. As illustrated, the system 10 includes a pulse oximeter 12 which is preferably connected to a patient (not specifically illustrated) via the patient's finger. The pulse oximeter 12 may be any of those commercially available, such as Model N100C/D/E/F manufactured by Nellcot, Inc., of Haywood, Calif., United States of America, or may be application specific. The pulse oximeter 12 measures both the pulse rate and the oxygen saturation $SaO_2$ of the patient. As is known, the pulse oximeter 12 works by measuring the amount of light absorbed through the skin, and correlates the measured data to pulse rate and oxygen saturation data standards. The pulse rate and oxygen saturation level data are then transferred to a microprocessor-based electronic control unit (ECU) 14. The ECU 14 preferably operates on power delivered from either an AC or DC power supply, lending portability to the oxydosimeter system 10 out of the typical hospital environment. The ECU 14 executes a control strategy, processing and analyzing the patient data to determine the proper amount of oxygen to deliver to the patient, as described in greater detail herein below.

With continuing reference to FIG. 1, the ECU 14 is in electrical communication with and controls a plurality of solenoid valves 20, 22, 24 and 26, such as the variably opening valve described in U.S. Pat. No. 5,008,773. The oxygen regulator-flowmeters 36, 38, 40 and 42, such as Model HMG-5SN commercially available from Thermodyne Industries, St. Louis, Mo., United States of America, are shown modified to include a plurality of solenoid valves which are connected to four adapters 28, 30, 32 and 34. The flowmeters and the adapters could be fabricated into a single unit. The regulator-flowmeters preferably test at one, two, three and four liters per minute (L/min) oxygen flow, respectively. As shown, one end of each regulator-flowmeter is preferably connected to a high pressure oxygen manifold 44, which is preferably in fluid communication with an oxygen source shown generally by reference numeral 46.

Each regulator-flowmeter delivers oxygen to the solenoid valves 20, 22, 24 and 26. Oxygen tubing, shown generally by reference numeral 48, extends from the solenoid valves and is distally fused into a single tube which is connected to nasal prongs 50. The nasal prongs 50, which preferably connect to the patient via the patient's nostrils, deliver oxygen to the patient at a varying rate (e.g. from 1 L/min to 4 L/min, in 1 L/min increments), as determined by the ECU 14.

The oxydosimeter system 10 may also be adapted for use with a simple aerosol mask (not specifically illustrated), which is utilized in place of the nasal prongs. The aerosol mask allows poorly humidified oxygen to flow at three, five, seven and nine L/min, respectively, through each of the regulator-flowmeters 36, 38, 40 and 42 of FIG. 1. The plastic oxygen tubing 48 preferably connects to four venturi valves set at 24%, 28%, 32% and 36% oxygen concentrations—all of which are connected to an aerosol mask.

It should be appreciated that any oxygen delivery system using standard nasal prongs may be converted into an oxydosimeter like the oxydosimeter 10. The flowmeter outlet of the standard oxygen delivery system is connected to a variably opening solenoid valve with a Coulomb controlling circuit, such as that disclosed in the '773 patent, by oxygen tubing. Oxygen tubing connects the valve, which is connected to the ECU, to the nasal prongs and the patient.

Figure 2A:
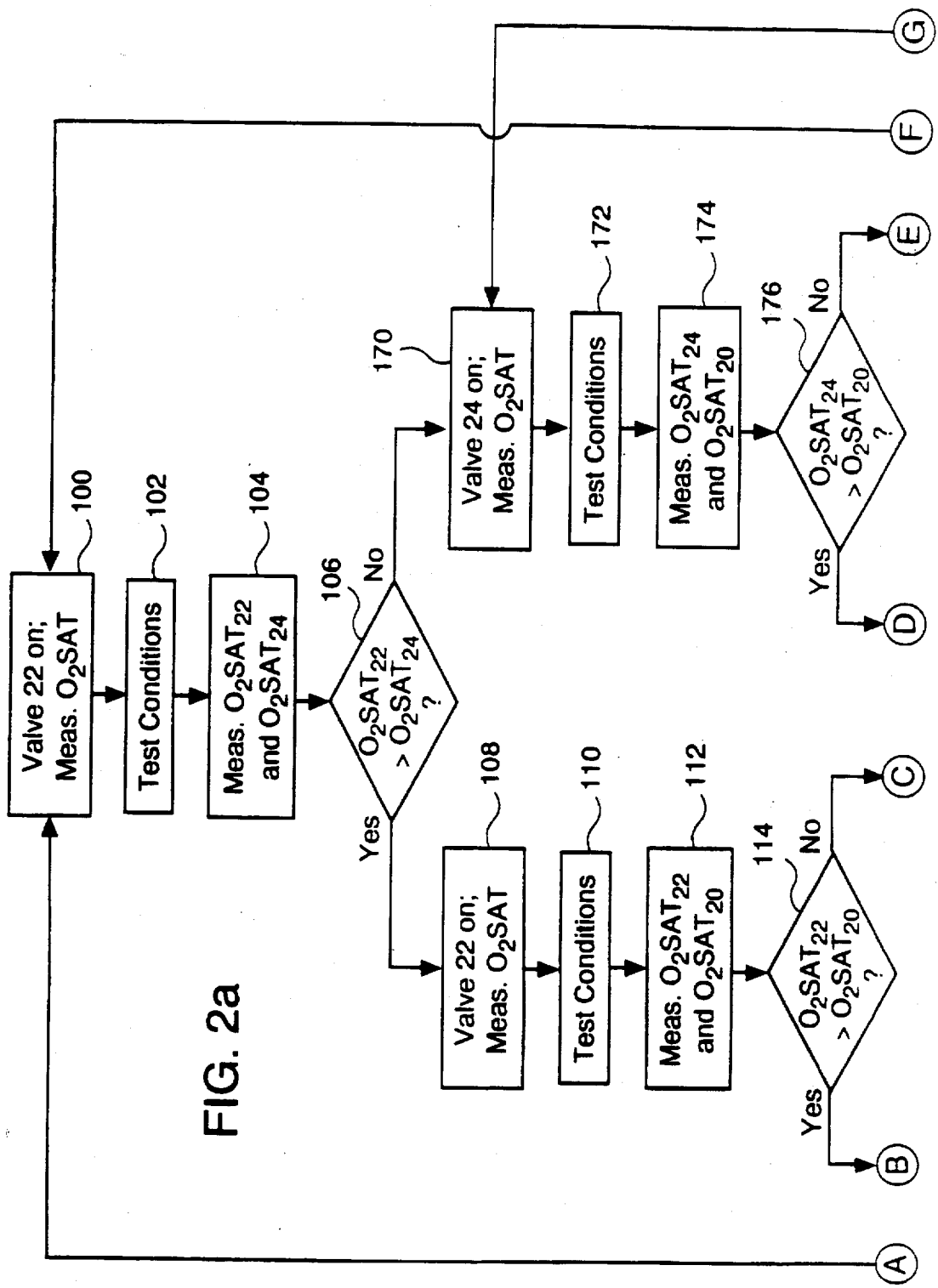
Figure 2D:
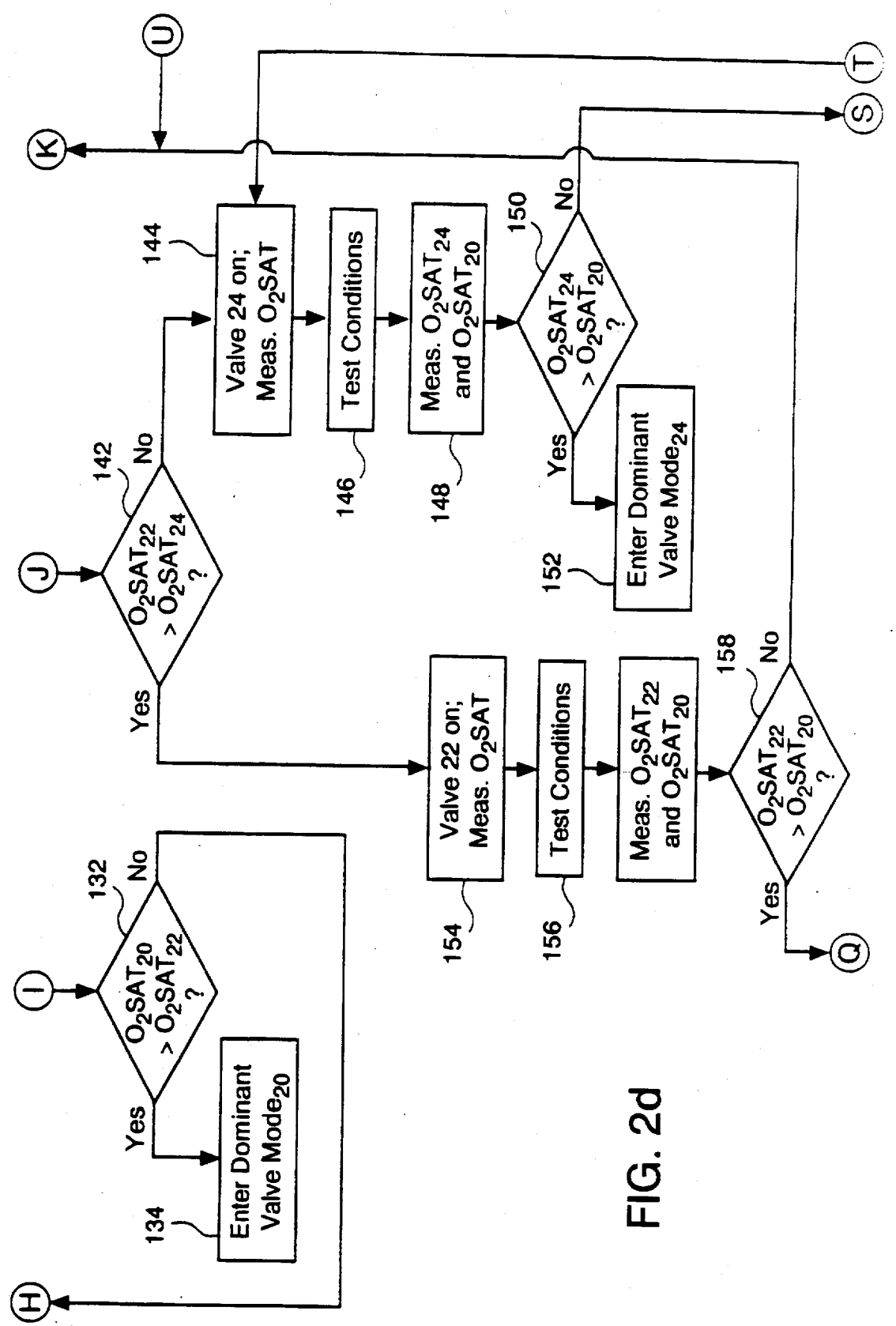
Figure 2E:
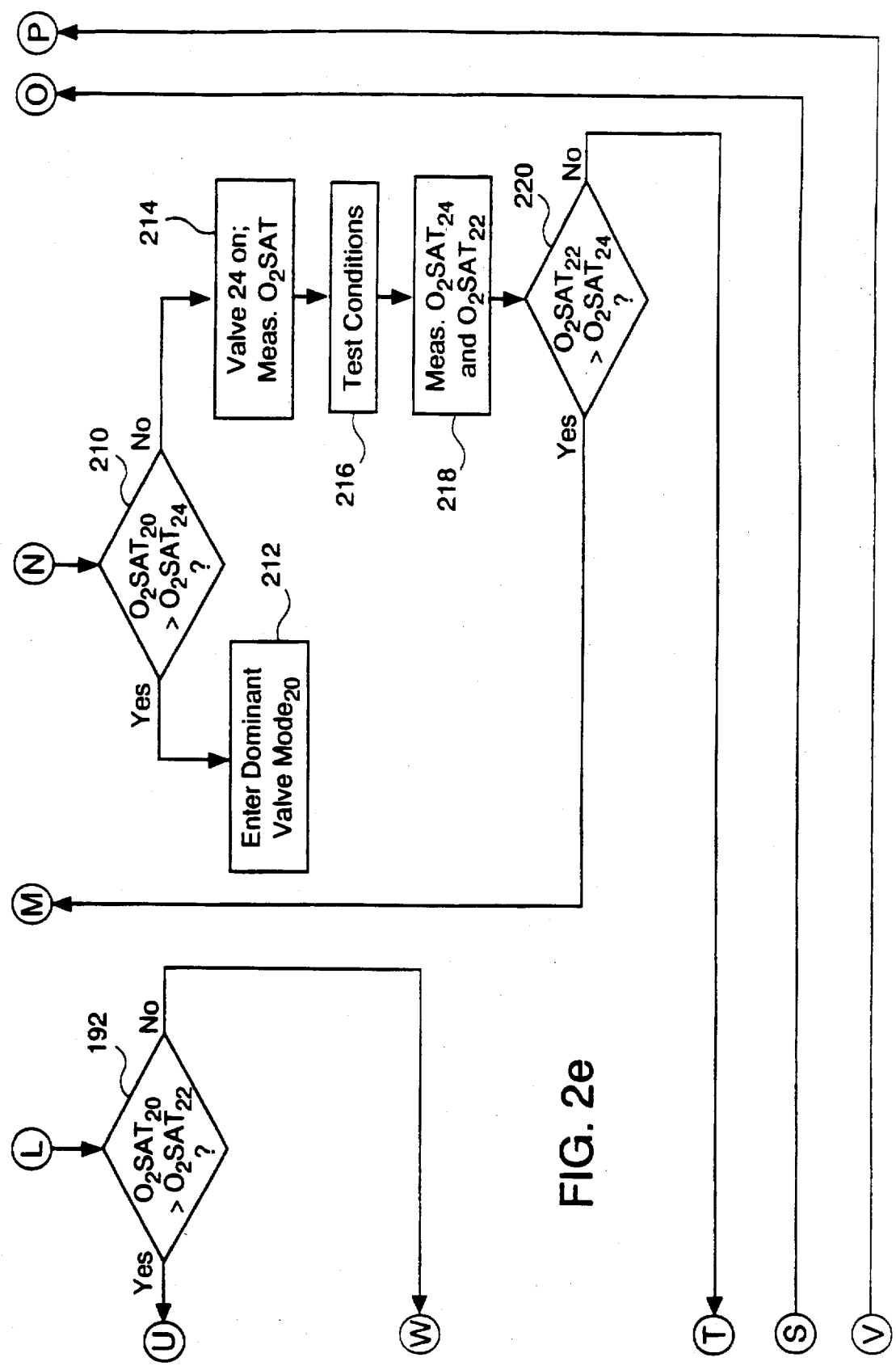
Figure 2F:
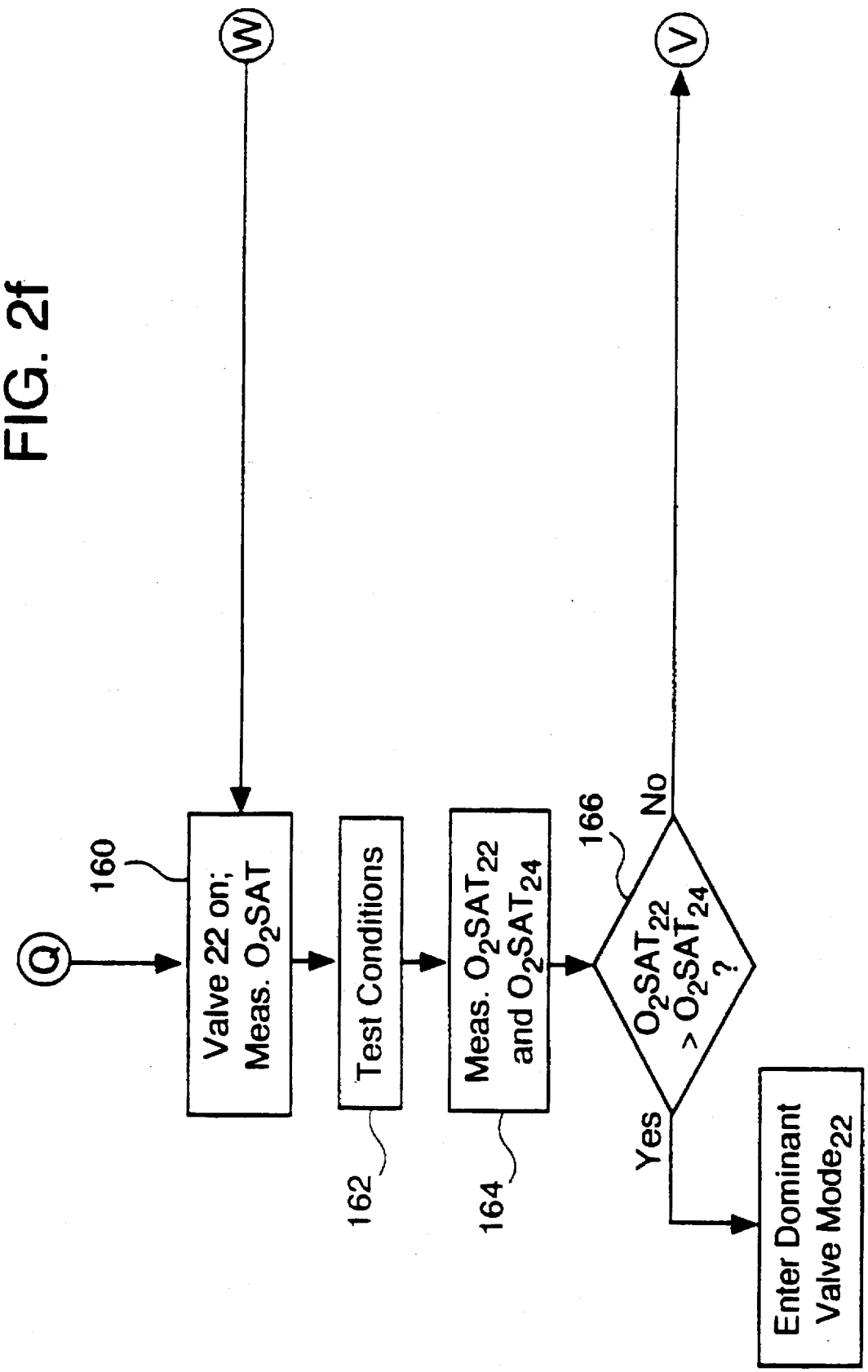

Referring now to FIGS. 2a–2f, there is shown a flowchart detailing the oxygenation strategy of the present invention for use with the adult COPD oxydosimeter 10 shown in FIG. 1. Generally, the strategy compares average oxygen saturation levels $SaO_2$ associated with the valves 20, 22, 24 and 26 as represented by variables $O_2SAT$ to determine the dominant valve—the valve which delivers oxygen to the patient to obtain the highest oxygen saturation level. The duration of each state shown is thirty seconds. As best shown in FIG. 2a, at step 100 the ECU energizes only valve 22, which is the dominant solenoid valve at that point, and measures $O_2SAT_{22}$ and $PRATE_{22}$ over a period of sixty seconds, the present average oxygen saturation and pulse rate associated with valve 22. These oxygen saturation and pulse rate values are then compared with the previous thirty (30) oxygen saturation and pulse rate values, which are stored in the memory of the ECU. If the present values of $O_2SAT_{22}$ and $PRATE_{22}$ are the highest, those values become the baseline values and valve 22 becomes the baseline valve for oxygen saturation and pulse rate. It should be appreciated that there could be one baseline valve for oxygen saturation and a different baseline valve for pulse rate. If the present values are not the highest, the highest values become the baseline values.

Figure 3:
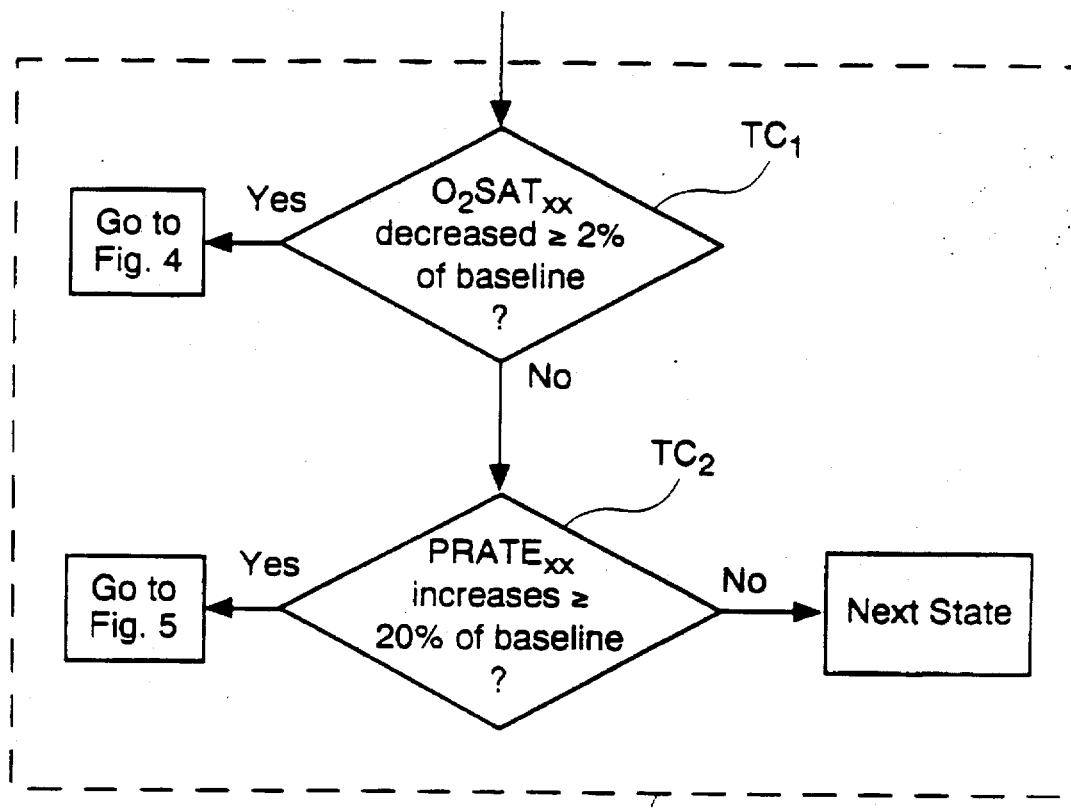
FIG. 3 is a detail of the Test Conditions box shown in FIG. 2, utilized by the present invention to determine entry into the Oxygen Saturation Exercise Mode and the Pulse Rate Exercise Mode.

With continuing reference to FIG. 2a, at step 102 a Test Conditions step is performed by the ECU. In the preferred embodiment, the Test Conditions step 102 actually consists of two steps, which are shown in greater detail in FIG. 3. Step 102 is applied to step 100 about every 5 seconds for the entire sixty second duration of the step 100. It should be noted that the step 100/step 102 combination is actually preferably a predetermined number of times prior to step 100. For example, step 100 could represent eleven (11) test conditions and twelve (12) sub-states. For ease of illustration and the sake of clarity, however, only one pair is actually illustrated. It should also be noted that the same representation could be utilized for each state in FIGS. 2a–2f and FIGS. 6–8. As best shown in FIG. 3, at step $TC_1$ (wherein XX=22), the ECU determines whether average $O_2SAT_{22}$ has decreased by an amount greater than or equal to about 2% of baseline oxygen saturation. If it has, control flow jumps to the Oxygen Saturation Exercise Mode, best shown in FIG. 4.

Figure 4:
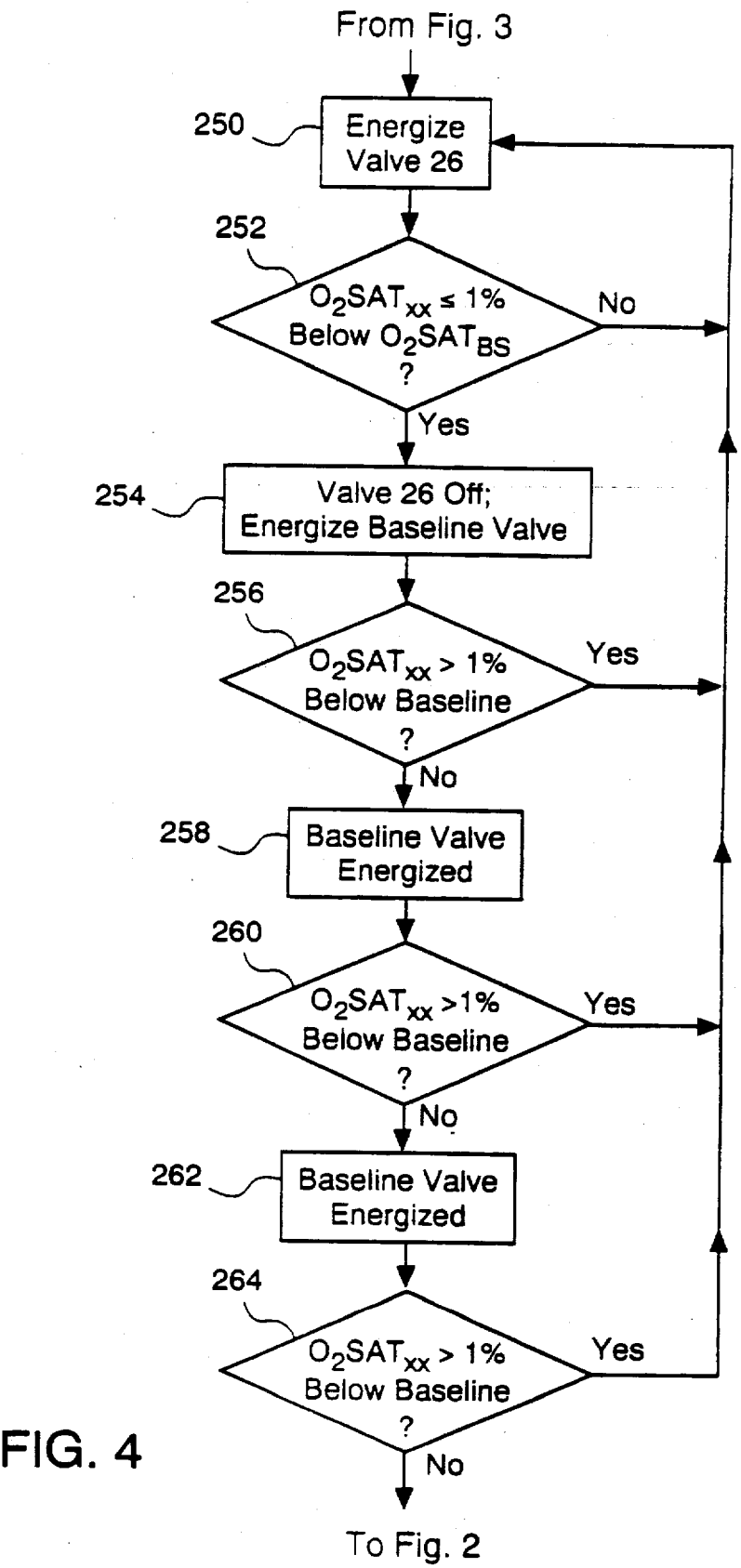
FIG. 4 is a flowchart detailing the Oxygen Saturation Exercise Mode of the oxygenation strategy of the present invention.

Referring now to FIG. 4, at step 250 of the Oxygen Saturation Exercise Mode, the ECU increases the amount of oxygen delivered to the patient by energizing valve 26, the 4 L/min valve. At step 252, the ECU measures $O_2SAT_{22}$ and determines whether the average oxygen saturation has increased to a value less than or equal to about 1% below the baseline oxygen saturation. If it has not, the patient continues to receive oxygen at a rate of 4 L/min. If the average oxygen saturation has so increased, at step 254 the ECU deenergizes the valve 26 and energizes the baseline valve, which delivers oxygen at a lower rate. At steps 256–264, this process is repeated to ensure maximal oxygenation.

Referring once again to FIG. 3, if the condition of step $TC_1$ is not satisfied, at step $TC_2$ (wherein XX=22 at this point) the ECU determines whether $PRATE_{22}$ has increased by an amount greater than or equal to about 20% of the baseline pulse rate. If the pulse rate condition is not satisfied, control flow returns to step 104 of FIG. 2a. If it has, control flow jumps to the Pulse Rate Exercise Mode, shown in FIG. 5.

Figure 5:
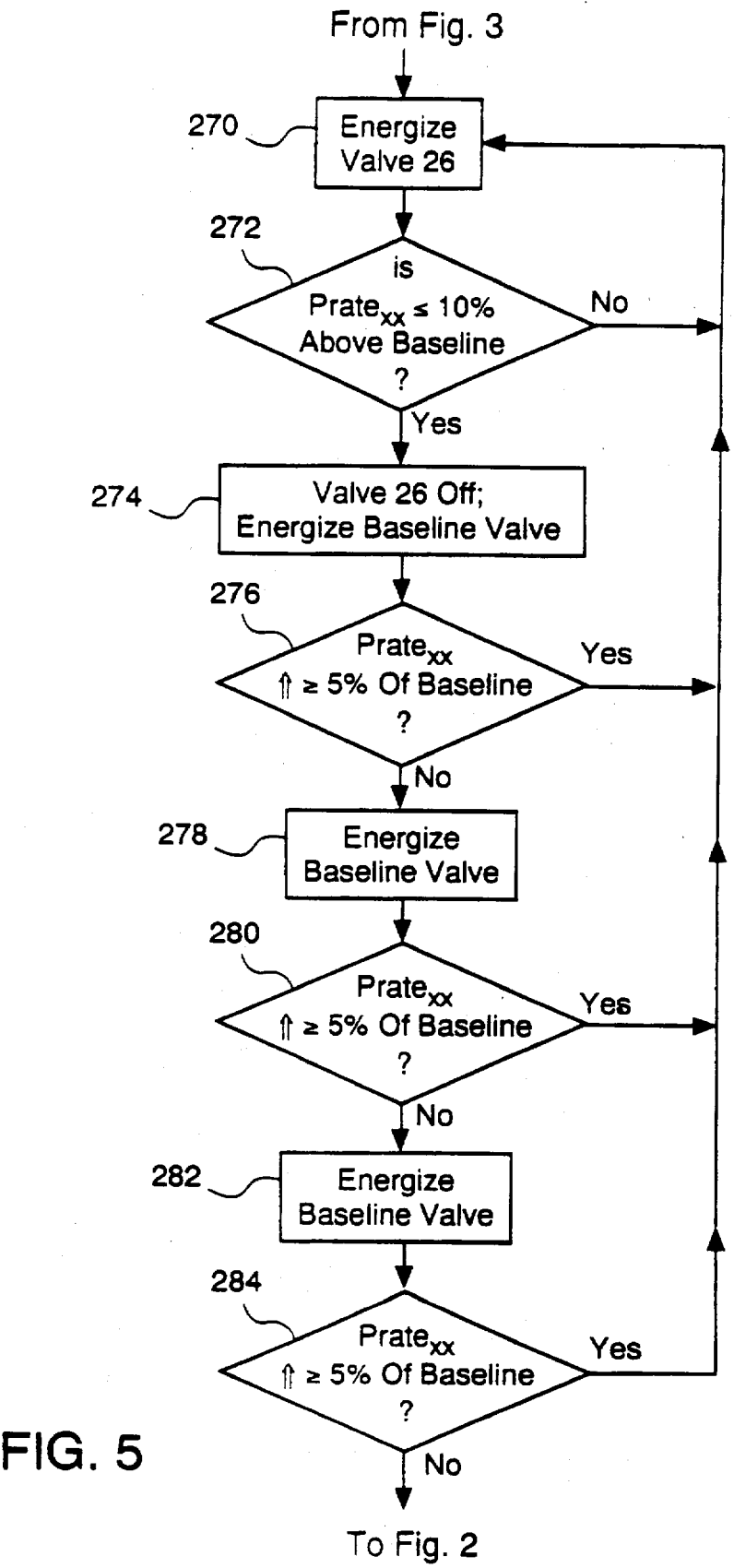
FIG. 5 is a flowchart detailing the Pulse Rate Exercise Mode of the oxygenation strategy of the present invention.

With reference to FIG. 5, at step 270 of the Pulse Rate Exercise Mode, the ECU increases the amount of oxygen delivered to the patient by energizing valve 26. At step 272, the ECU measures $PRATE_{26}$ and determines whether the patient's average pulse rate has decreased to a value that is less than or equal to about 10% above the baseline pulse rate. If it has not, the patient continues to receive oxygen at a rate of 4 L/min, in an attempt to lower the average pulse rate. If the pulse rate has so decreased, at step 274 the ECU deenergizes the valve 26 and energizes the baseline valve, which delivers oxygen at a lower rate. At step 276, the ECU determines whether the average pulse rate increases, due to the change in oxygen delivery, by an amount that is greater than or equal to about 5% of the baseline pulse rate ($PRATE_{BS}$). If it has, the baseline valve is deenergized and valve 26 is energized to once again lower the pulse rate. If the pulse rate has not increased when the baseline valve was energized, at step 278 the ECU maintains energization of the baseline valve. At steps 280–284, this process is repeated to insure maximal oxygenation.

With continuing reference to FIG. 2, at step 104 the ECU again measures average $O_2SAT_{22}$, but over a thirty second period. The ECU then deenergizes valve 22 and energizes valve 24. Thirty seconds later, the ECU measures $O_2SAT_{24}$, the average oxygen saturation in the patient associated with operation of the valve 24. At step 106, the ECU compares these measured oxygen saturations. If $O_2SAT_{22} > O_2SAT_{24}$, valve 22 remains the dominant valve. The ECU energizes valve 22 and deenergizes valve 24 and control flow jumps to step 108–114, wherein the process defined by steps 100–106 are repeated to determine dominance between valve 22 and valve 20 based on the average oxygen saturations associated with the valves.

With continuing reference to FIG. 2a, at step 108 valve 22 is energized and after sixty seconds the ECU measures average $O_2SAT_{22}$ and $PRATE_{22}$. The ECU then compares the present $O_2SAT_{22}$ and $PRATE_{22}$ to the previous thirty oxygen saturations and pulse rates. If the present $O_2SAT_{22}$ and $PRATE_{22}$ values are the highest, the present values become the baseline values. If the present values are not the highest, the highest values become the baseline values. At step 110, the ECU performs the Test Conditions (previously described and shown in FIG. 3, wherein XX=22). Preferably, one test condition is repeated every five (5) seconds as described. If the condition of step $TC_1$ of FIG. 3 is satisfied, the Oxygen Saturation Exercise Mode is carried out, as shown in FIG. 4 and described in greater detail above. If the condition of step $TC_2$ of FIG. 3 is satisfied, the Pulse Rate Exercise Mode is carried out, as shown in FIG. 5 and described in greater detail above. If none of the twelve test conditions at steps $TC_1$ and $TC_2$ are satisfied, control flow returns to step 112 of FIG. 2a.

With continuing reference to FIG. 2a, at step 112 the ECU first measures the present oxygen saturation associated with valve 22 over a thirty second period. The ECU then deenergizes valve 22, energizes valve 20, and measures the average oxygen saturation associated with valve 20 ($O_2SAT_{20}$) after thirty seconds. At step 114, the ECU determines whether the present $O_2SAT_{22}$ is greater than the present $O_2SAT_{20}$. If it is, valve 22 remains the dominant valve. Since valve 22 is the dominant valve for three consecutive intervals, valve 22 has complete dominance and the Dominant Valve Mode is entered at step 116, as shown in FIG. 2b.

Figure 6:
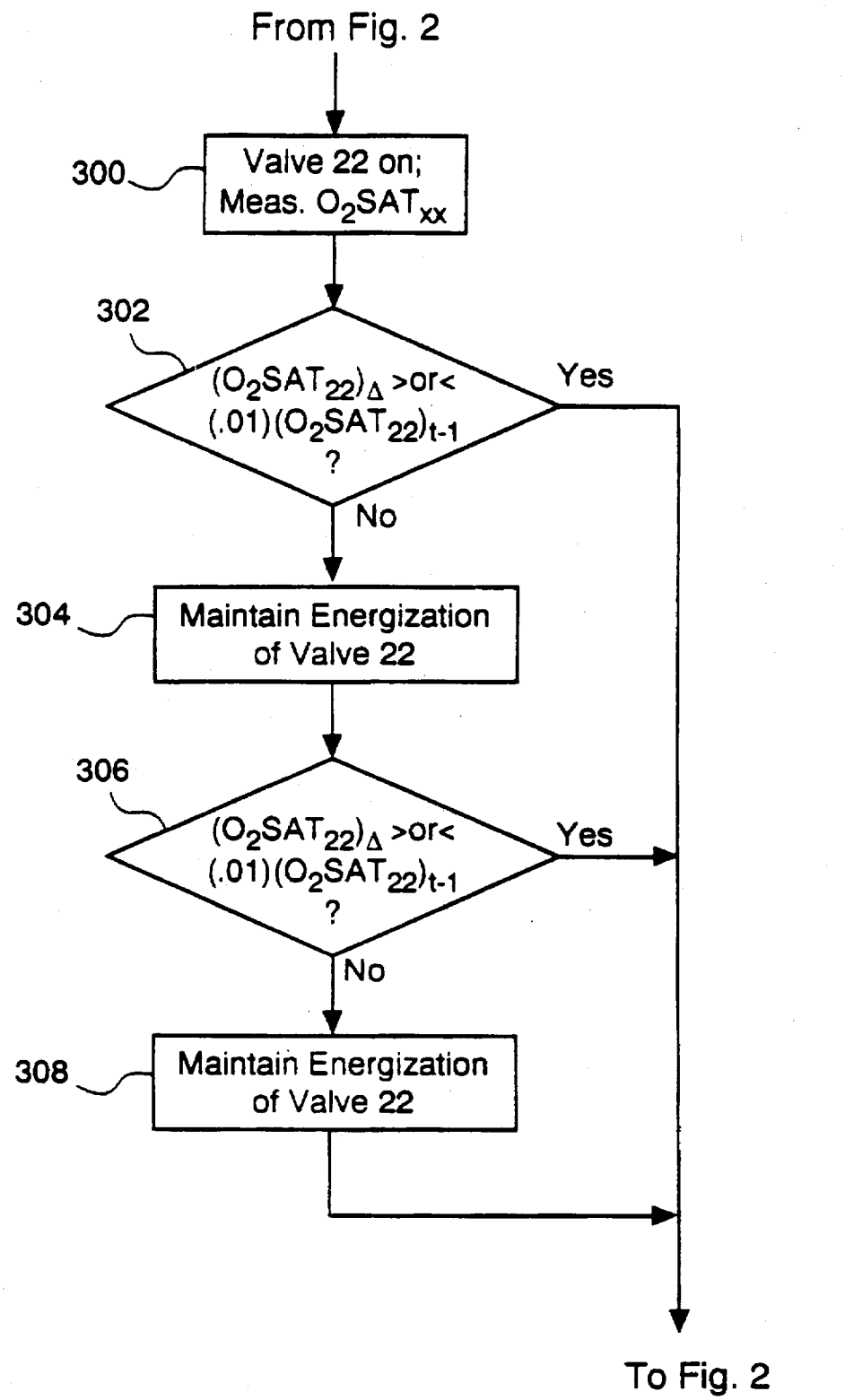
FIG. 6 is a flowchart detailing the Dominant Valve Mode oxygenation strategy utilized by the present invention when valve 22 of FIG. 2 is completely dominant.

Referring now to FIG. 6, there is shown a flowchart detailing the Dominant Valve Mode of the oxygenation strategy of the present invention. During this mode, the ECU monitors the oxygen saturation level at thirty second intervals as the patient receives oxygen from the dominant valve (i.e. valve 22). If the oxygen saturation level changes by more than a predetermined amount between intervals, Dominant Valve Mode$_{22}$ is exited and control returns to FIG. 2.

As shown in FIG. 6, the first step of the Dominant Valve Mode is to energize the dominant valve and begin measuring average oxygen saturation levels ($O_2SAT_{22}$) at thirty second intervals. At step 302, the ECU determines whether $(O_2SAT_{22})_A$, which represents the difference between the present oxygen saturation level, $(O_2SAT_{22})_p$ and the previous oxygen saturation level, $(O_2SAT_{22})_{p-1}$, is greater than or less about 1% of the previous $(O_2SAT_{22})_{p-1}$. Thus, the ECU is monitoring for a certain degree of change in the average oxygen saturation level. If the average oxygen saturation level has so changed over a thirty (30) second period, control flow jumps back to FIGS. 2a–2f for a determination of valve dominance as previously described. If the oxygen saturation level has not changed by the requisite amount, at step 304 the ECU maintains energization of valve 22 for a predetermined number of consecutive thirty (30) second intervals. In the preferred embodiment, valve 22 remains energized for twenty (20) intervals (i.e. about 10 minutes). Thereafter, at step 306, the ECU again determines whether $(O_2SAT_{22})_A$ is greater than or less about 1% of $(O_2SAT_{22})_{p-1}$. If the oxygen saturation level has so changed, control flow jumps back to step 100 of FIG. 2 for a determination of valve dominance as described in greater detail above. If the oxygen saturation level has not changed by the requisite amount, at step 308 the ECU maintains energization of valve 22 and measures oxygen saturation after a thirty second period, prior to returning to FIG. 2 at step 100 for a determination of valve dominance as described in greater detail above. At step 300, 304 and 308, every five seconds for thirty seconds per step, the ECU performs the Test Condition of FIG. 3. If the condition is satisfied, the Oxygen Saturation Exercise Mode of FIG. 4 is executed, as described in greater detail above. If the condition of step $TC_2$ is satisfied, the Pulse Rate Exercise Mode of FIG. 5 is executed. If neither of the test conditions are satisfied, control jumps back to step 100, 118 or 170 of FIGS. 2a–2f.

Figure 7:
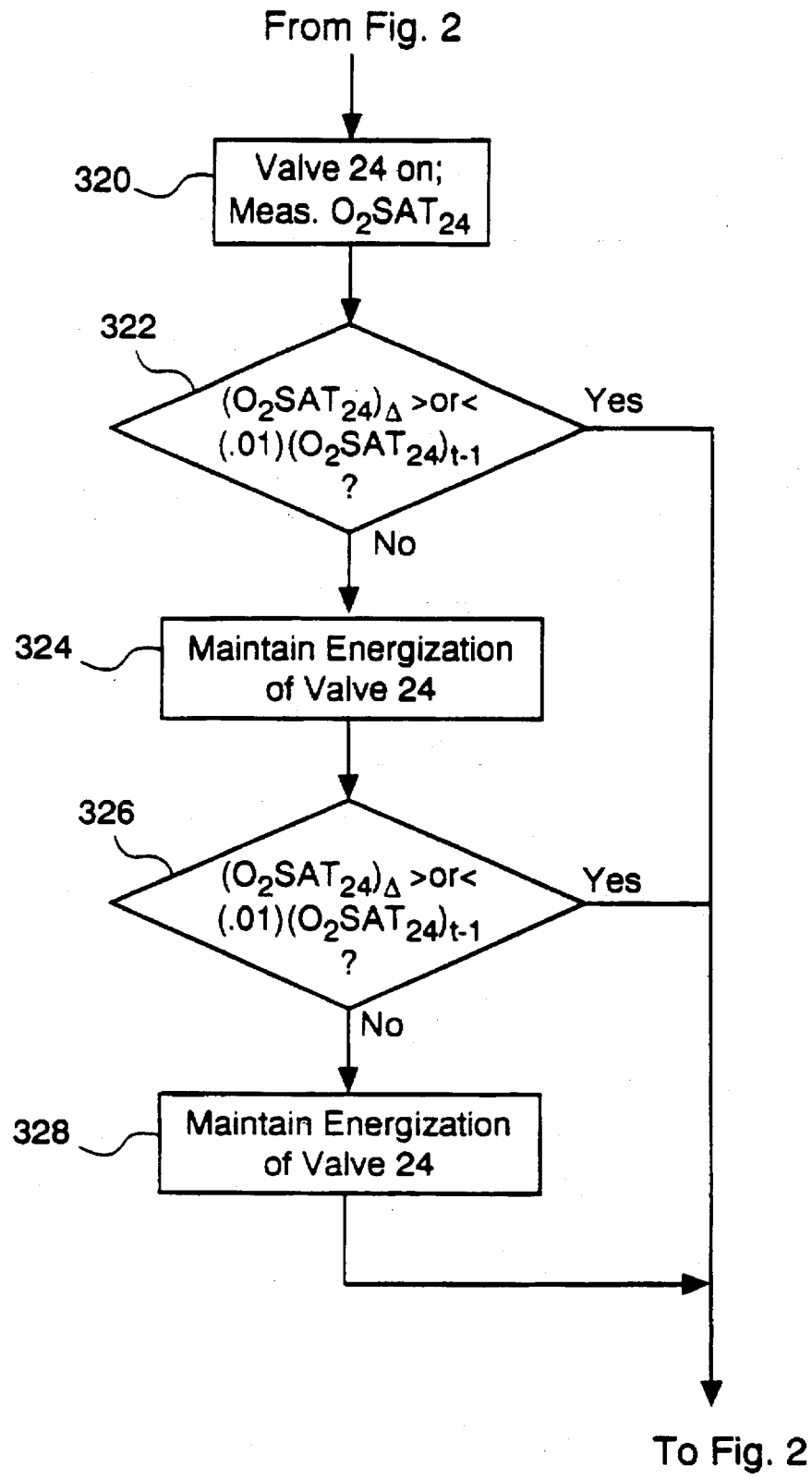
FIG. 7 is a flowchart detailing the Dominant Valve Mode oxygenation strategy utilized by the present invention when valve 24 of FIG. 2 is completely dominant.
Figure 8:
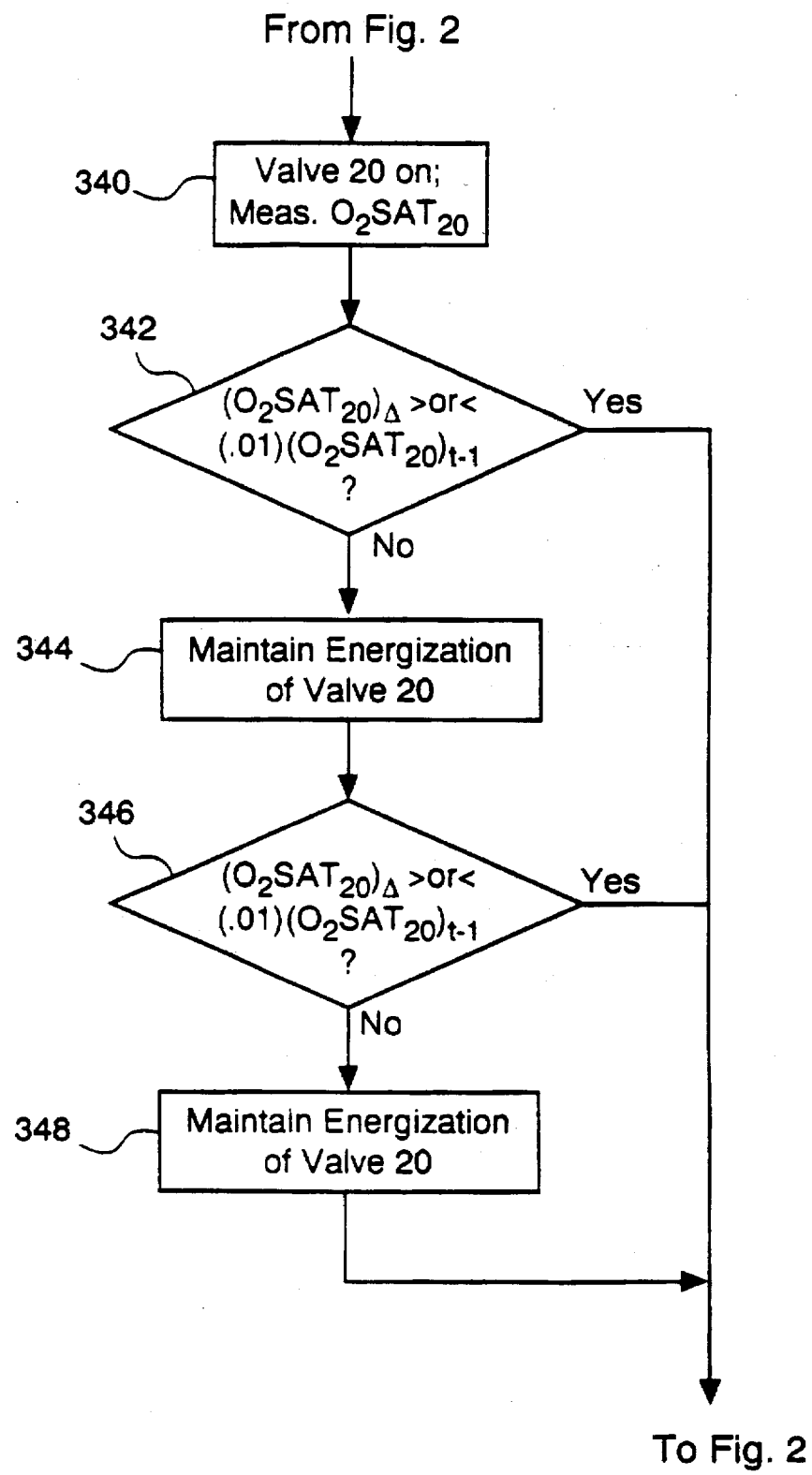
FIG. 8 is a flowchart detailing the Dominant Valve Mode oxygenation strategy utilized by the present invention when valve 20 of FIG. 2 is completely dominant.

Referring once again to FIGS. 2b–2f, it can be seen that the remainder of the flowchart consists of the steps described above arranged in a generally repetitive pattern. As previously described, these steps compare pairs of valves to determine complete dominance, which is achieved when the same valve dominates the other valves for three consecutive test intervals. For example, at step 100 valve 22 is the dominant valve. If valve 22 dominates valve 24 (decided at step 106) and valve 22 dominates valve 20 (decided at step 114), then valve 22 is completely dominant and the Dominant Valve Mode of FIG. 5 is entered at step 116. A similar result for valve 22 could be achieved through the branch identified by steps 142, 158 and 166, or through the branch identified by steps 184, 192 and 166. It should be appreciated therefore, that valve 24 could be the dominant valve if it dominates for three consecutive intervals. For example, if valve 24 first dominates valve 22 (decided at step 106), then dominates valve 20 (decided at step 176) and lastly dominates valve 22 again (decided at step 184), valve 24 is completely dominant and the Dominant Valve Mode for valve 24, shown in FIG. 7, is entered at step 194. Steps 320–328 of FIG. 7 are substantially similar to steps 300–308 of FIG. 6, which were described in greater detail above. A similar result for valve 24 could be achieved through the branch identified by steps 124, 142 and 150, or by the branch identified by steps 210, 220 and 150. Similarly, it should be appreciated that valve 20 could be the dominant valve if it dominates for three consecutive intervals. For example, if valve 20 first dominates valve 22 (decided at step 114), then dominates valve 24 (decided at step 124) and lastly dominates valve 22 again (decided at step 132), valve 20 is completely dominant and the associated Dominant Valve Mode is entered at step 134. A similar result for valve 20 could be achieved through the branch identified by steps 176, 202 and 210, or through the branch identified by steps 192, 124 and 132. Steps 340–348 of FIG. 8 are substantially similar to steps 320–328 of FIG. 7 and steps 300–308 of FIG. 6, which were described in greater detail above. It should be noted that, with reference to FIG. 7, when leaving the dominant valve mode of valve 24, control flow jumps back to step 170 of FIG. 2a and that, with reference to FIG. 8, when leaving the dominant valve mode of valve 20, control flow jumps back to step 118 of FIG. 2b. Finally, the upper test condition of FIG. 3 (i.e. $TC_1$) is preferably present between every state in FIG. 4 (except step 250) and FIG. 5, and is exercised every five seconds for each state, as described above. If the condition is not satisfied, control flow jumps to the next state.

Neonatal Nasal Prong Oxydosimeter

Figure 9:
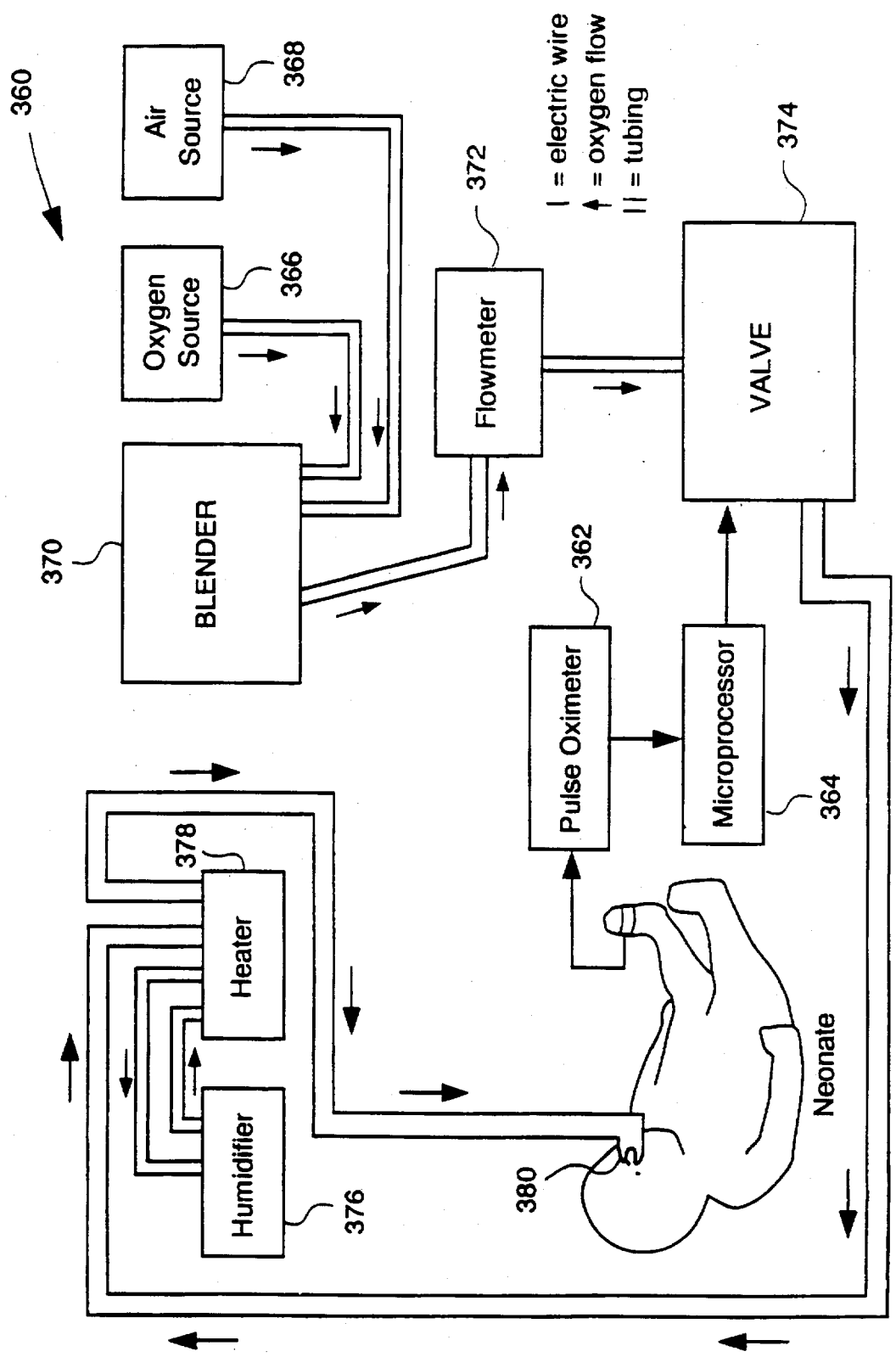
FIG. 9 is a block diagram of a second embodiment of the present invention for use as a neonatal nasal prong oxydosimeter.

Referring now to FIG. 9, a second embodiment of the present invention is shown. This embodiment, indicated generally by reference numeral 360, is particularly suited for use as a Neonatal Nasal Prong Oxydosimeter. As illustrated, oxydosimeter 360 includes a pulse oximeter 362 for attachment to a neonate, preferably to the foot of the neonate, as shown. Pulse oximeter 362 supplies oxygen saturation data to the microprocessor 364, which executes a control strategy to maintain oxygen saturation levels in a predetermined narrow range of acceptable values or at an acceptable discrete level, as described in greater detail below.

With continuing reference to FIG. 9, the Neonatal Nasal Prong Oxydosimeter 360 also includes a pressurized oxygen source 366 and a pressurized air source 368, both of which are in fluid communication with a blender 370, such as the 3800 Microblender commercially available from Bird Products Corporation. Blender 370 preferably provides oxygen at 100% concentration to a flowmeter 372, such as Model 0-3, commercially available from the Timeter Corporation, Lancaster, Pa., United States of America. The output from flowmeter 372 is supplied to a valve, shown generally by reference numeral 372, which is controlled by microprocessor 364 to dispense proper amounts of oxygen to the neonate.

In a preferred embodiment of the present invention, the output from flowmeter 372 is adjusted to provide 1 L/min. Valve 374 is a 33 increment, variably opening solenoid valve with a coulomb controlling circuit, such as that disclosed in the '773 patent. The lowest controllable flow rate is 0.03 L/min. As shown, oxygen from valve 374 is delivered through tubing to a humidifier 376 and an optional heater 378, prior to being delivered to the neonate via nasal prongs 380.

Figure 10:
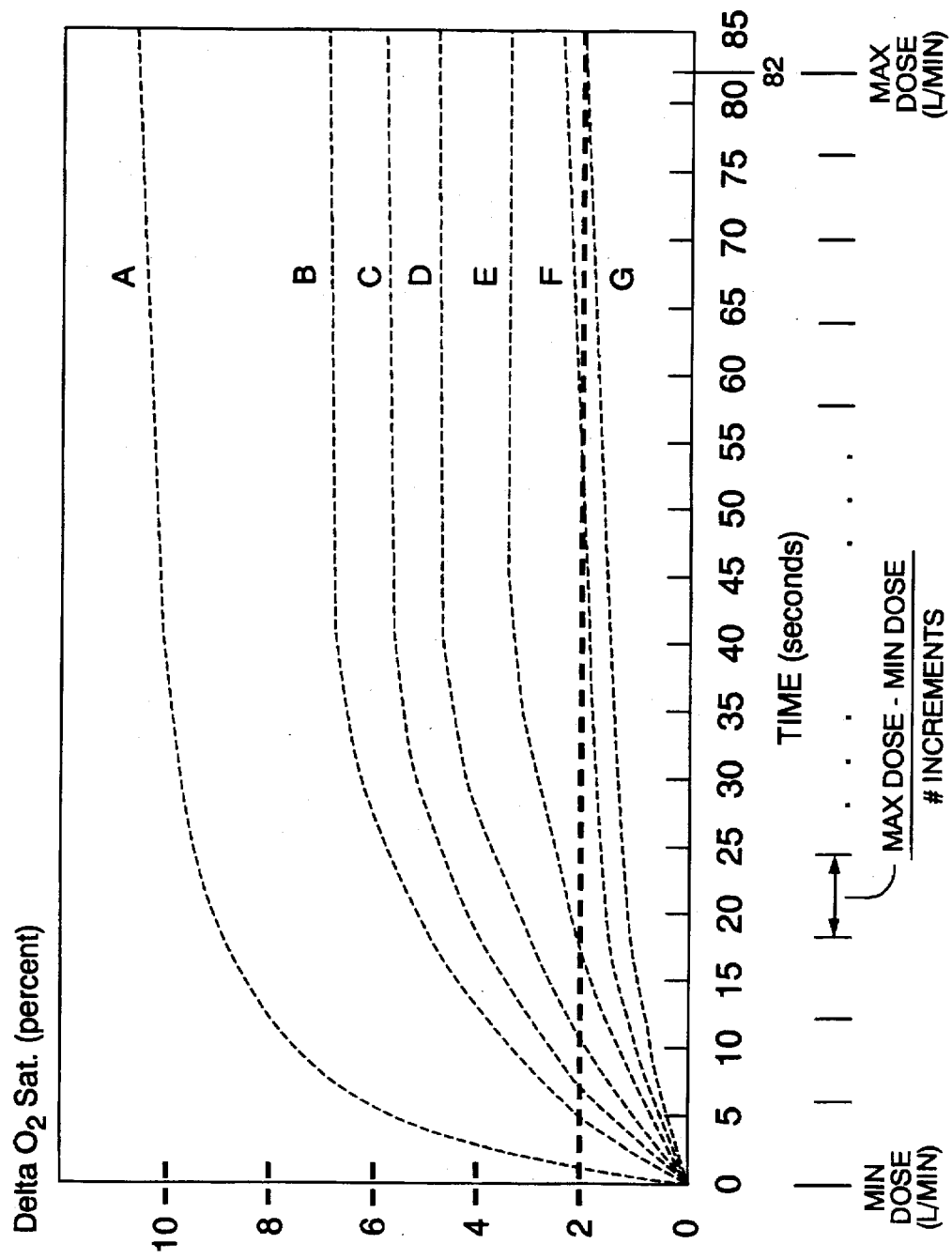
FIG. 10 is a graphical representation of representative physiological response curves used to select a proper oxygen dose according to the present invention.

Referring now to FIG. 10, a graph used to determine an appropriate oxygen dose to effect a desired change in the blood oxygen saturation level of a particular patient, and to maintain the corresponding blood oxygen saturation level, is shown. This graph is utilized in deriving the flow sheets (discussed below) of various embodiments of the present invention. The graph of FIG. 10 is utilized for the Neonatal Nasal Prong Oxydosimeter embodiment, discussed immediately above, as well as embodiments for use as a Neonatal Oxyhood Oxydosimeter, an Adult Fully Automatic Respirator, an Adult Fully Automatic Oxygenator, a Neonatal Fully Automatic Respirator, and a Fully Automatic CPAP Device.

Curves A through G of FIG. 10 depict oxygen dose response curves for seven (7) representative subjects illustrating changes in blood oxygen saturation level in response to a particular (maximum available) administered oxygen dose (or concentration, as explained below) over time. The curves are determined empirically, but approximate logarithmic curves, over a period of about 82 seconds. This time period may vary depending upon the particular oxygenation system and the particular subject being treated. Available oxygen doses for the particular oxygenation system being utilized are evenly distributed below the time axis, as shown. For example, in the Neonatal Nasal Prong Oxydosimeter embodiment, the doses preferably range from 0.03 L/min to 1.0 L/min in 33 equal increments.

Determination of an appropriate oxygen dose for a particular subject (a neonate, for example) utilizing a particular oxygenation system (the Neonatal Nasal Prong Oxydosimeter embodiment of the present invention, for example) using FIG. 10, proceeds as follows. Assume the neonate of this example has a blood oxygen saturation level of 88% and the desired blood oxygen saturation level is 90%. Thus, the desired delta $O_2$ saturation is 2%, as represented by the dashed line of FIG. 10. The maximum oxygen dose (1.0 L/min in this case) is administered for a period of about 82 seconds while monitoring the blood oxygen saturation level of the neonate to produce an oxygen dose response curve. Preferably, the blood oxygen saturation level is centrally monitored (at the pulmonary vein) to eliminate circulation delay. Assume the physiological response of the neonate produces a curve similar to curve G. The point where curve G intersects the dashed line determines the dose necessary to maintain the desired blood oxygen saturation level (90% in this example).

As a further illustration, assume the same conditions as above with the exception being that the physiological response of the neonate to the 1 L/min dose produced a curve similar to curve E in FIG. 10. Curve E intersects the delta 2% curve at about t=20 seconds. This corresponds to the 8th possible dose increment, since each dose increment spans about 2.5 seconds (82 seconds/33 increments=2.48 seconds per increment). Since the minimum dose is 0.03 L/min, the 8th dose increment would be 0.24 L/min. Thus, to maintain the desired blood oxygen saturation level of 90%, a dose of 0.24 L/min should be administered for this neonate.

Of course, the maximum possible blood oxygen saturation level is 100%. Thus, desired delta $O_2$ saturation levels should be chosen appropriately. If the $O_2$ saturation level is monitored peripherally (at the arm or leg), the curves of FIG. 10 would be shifted by about 5.1 seconds to the right due to circulation delay, i.e. the time lag between oxygenation response of the lungs and the corresponding response of the peripheral circulation. Thus, the response curve should be appropriately offset so that the beginning of an increase in blood oxygenation level at the monitoring point corresponds to time t=0.

Since it is desirable to maintain a relatively constant blood oxygen saturation level $SaO_2O$ for a particular subject, it is often necessary to decrease $SaO_2$ rather than increase $SaO_2$. The graph of FIG. 10 is utilized only when a positive delta $SaO_2$ is desired. However, an analogous graph may be generated which depicts a decrease in $O_2SAT$ for a particular subject. The analogous graph would then be used in a similar fashion to determine the proper oxygen dose to administer.

Although some subjects can not tolerate the maximum flow rate of the particular oxygenation system being utilized, a graph similar to the graph of FIG. 10 may still be used to determine the proper oxygen dose. Instead of using the maximum dose available for the particular oxygenation system, a lesser dose, which the subject can tolerate, is used in its place. For example, some small neonates can not tolerate a 1 L/min flow rate. Thus, the 0–1 L/min range may be divided into a number of dose ranges. For example, if two (2) ranges are being utilized, the first range would include rates from 0.03 L/min to 0.51 L/min and have 17 equal increments spanning about 4.8 seconds each. The second range would include rates from 0.54 L/min to 1.0 L/min and have 16 equal increments spanning about 5.1 seconds each. This effectively doubles the response time from 82 to 164 seconds. Thus, the "maximum" rate used to determine the proper dose rate, corresponding to 82 seconds on the time axis of FIG. 10, is 0.51 L/min. The proper oxygen dose rate to administer is then determined as described above.

Before describing the flow charts which illustrate the system and method of the present invention for automatically selecting a proper oxygen dose rate, it is useful to explain the terminology employed. In general, it is desirable to achieve a base state. A "base state" represents an oxygen dose rate which is delivered to the subject such that the subject has attained the desired $O_2SAT$ and is relatively stable. Once a base state is entered, it continues to be referred to as the current base state until a subsequent base state is entered, i.e. when searching for a more desirable base state, the current base state is the most recent base state attained. The "current dose" represents the oxygen dose rate which is currently being administered to the subject. An ECU, such as ECU 14, selects the appropriate combination of valves, or the appropriate valve setting to effect delivery of the current dose. A "possible dose" represents one of the oxygen dose rates available to be administered, but is not being currently administered. The following discussion assumes a number of discrete dose rates which may be divided into a number of discrete ranges. However, the system and method could easily be adapted for use with a system having continuously variable dose rates.

Current pulse oximeters are subject to electrical artifact (noise) which may distort $SaO_2$ measurements. The shorter the duration of the shortest series state, the greater the effect of electrical artifact. To reduce the effect of electrical artifact on the system performance, a new parameter called Mondry's mean may be used. Mondry's mean reduces electrical artifact and retains much of the statistical behavior of the true mean. Mondry's mean is determined by taking the arithmetic mean of the samples after filtering the samples to eliminate spurious readings. The filter is essentially a band pass filter centered about the median of the samples in the measurement interval. The bandwidth of the bandpass filter (equal to ±1 Mondry's deviation) is based on the characteristics of the system. In a preferred embodiment, Mondry's deviation is equal to 3% $SaO_2$ so the bandwidth of the filter is ±3% $SaO_2$. Thus, any sample values which are more than 3% above or below the median are not used in calculating Mondry's mean. Mondry's mean will be used to measure oxygen saturation in the later defined base states.

For the various embodiments of the present invention, either the median, or preferably Mondry's mean, will be the parameters used for calculating base state oxygen saturation values, depending upon the current operating conditions. Improvements in transducer technology may obviate the need for Mondry's mean and allow use of the true arithmetic mean. However, if a conventional pulse oximeter is utilized, Mondry's mean should be used during the oxygen saturation of base states. During adjustment states and washout states, the pulse oximeter measurement is not processed. During all other states, except base states, $O_2SAT$ is determined utilizing pulse oximeter measurements over the most recent three (3) heartbeats per interval as follows. Similar to Mondry's mean, a bandpass filter centered about the median and having a bandwidth of ±1 Mondry's deviation is applied to the three measurements to eliminate spurious measurements due to electrical artifact, or other such distortions. Preferably, the most recent measurement within ±1 Mondry's deviation of the median is used. Otherwise, the median of the three (3) measurements is used.

Thus, the shortest operating state should contain at least three (3) measurements. Preferably, the shortest state is about 2.6 seconds. This corresponds to a heart rate of at least 72 beats per minute. In some of the embodiments discussed below, patients will generally experience lower heart rates than with other embodiments, such as the Neonatal Nasal Prong Oxydosimeter. As a result, in the presence of significant electrical artifact, Mondry's mean could possibly eliminate the measurements for a particular operating state if less than three (3) measurements are recorded. In this case, all embodiments, except those mentioned above, utilize the most recently recorded oxygen saturation value which was within ±1 Mondry's deviation of the median. As long as there are an odd number of at least three (3) measurements in an interval, elimination by Mondry's mean of all the measurements will not occur.

It is still possible to use the various embodiments of the present invention with patients having a heart rate below about 72 beats per minute by utilizing a number of ranges or tiers. To compensate for lower heart rates, longer intervals are provided for measurements. As discussed below for the Neonatal Nasal Prong Oxydosimeter, dividing the available doses into 2 tiers or ranges, effectively doubles the response time from about 82 seconds to about 164 seconds. Thus, the shortest interval also doubles from about 2.6 seconds to about 5.2 seconds so as to accommodate heart rates as low as 36 beats per minute.

Referring now to FIGS. 11a–11e, flow charts are shown which illustrate the system and method for automatic selection of the proper oxygen dose rate according to the present invention. Step 400 determines various system parameters which may be predetermined and stored in memory, calculated by an ECU (such as ECU 14), or entered by a system operator. The system parameters include the following:

N—number of available ranges $min_R$—minimum dose for each range $max_R$—maximum dose for each range $I_R$—available dose increments for each range $O_2SAT$—current blood oxygen saturation level $SaO_2$ $T_{O2}$—desired blood oxygen saturation level $SaO_2$ $A_L$—low $O_2SAT$ alarm threshold $A_H$—high $O_2SAT$ alarm threshold $\delta_L$—low base state threshold $\delta_H$—high base state threshold $\tau_{ss}$—series state delay time $\tau_{CIRC}$—circulation delay time $\tau_{WASH}$—washout delay time $t_r$—desired response time (about 82 seconds)

Figure 11A:
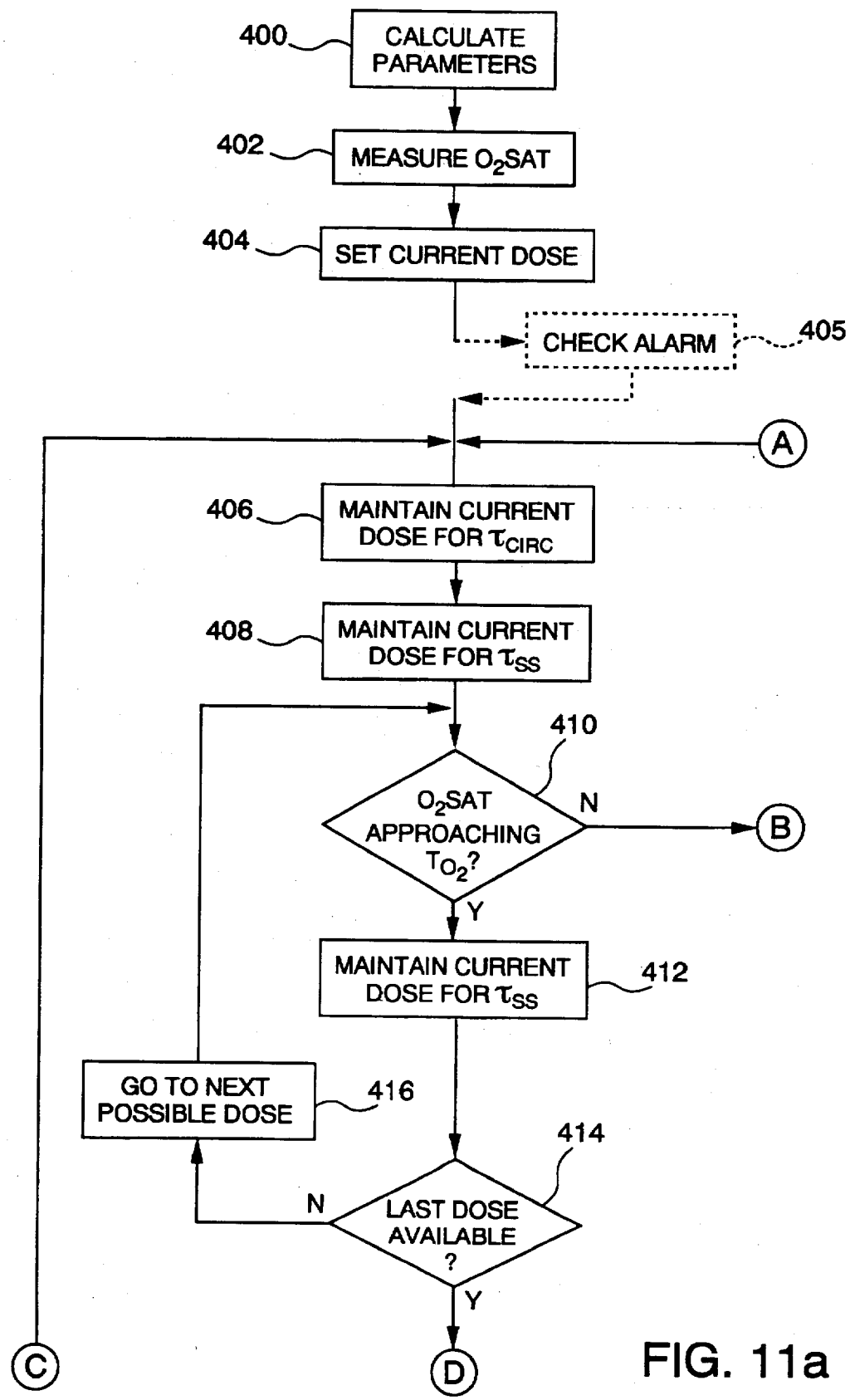
FIGS. 11a–11e are flow charts illustrating the system and method for automatically selecting a proper oxygen dose and maintaining the selected dose within predetermined limits according to the present invention.

As shown in FIG. 11a, step 402 determines $O_2SAT$ (using Mondry's mean) over a 5 second measurement interval. The ECU uses $O_2SAT$ and $T_{O2}$ to calculate an anticipated dose response curve which would achieve $T_{O2}$ in time $t_r$ (using a logarithmic approximation as described above). Preferably, $t_r$ is about 82 seconds. This anticipated dose response curve is stored in memory for future reference. It is interesting to note that the system and method of the present invention is not limited to a logarithmic response curve. The present invention would work well with a number of other functions which may be plotted in Quadrant I (upper right quadrant) in a cartesian coordinate system.

Figure 12:
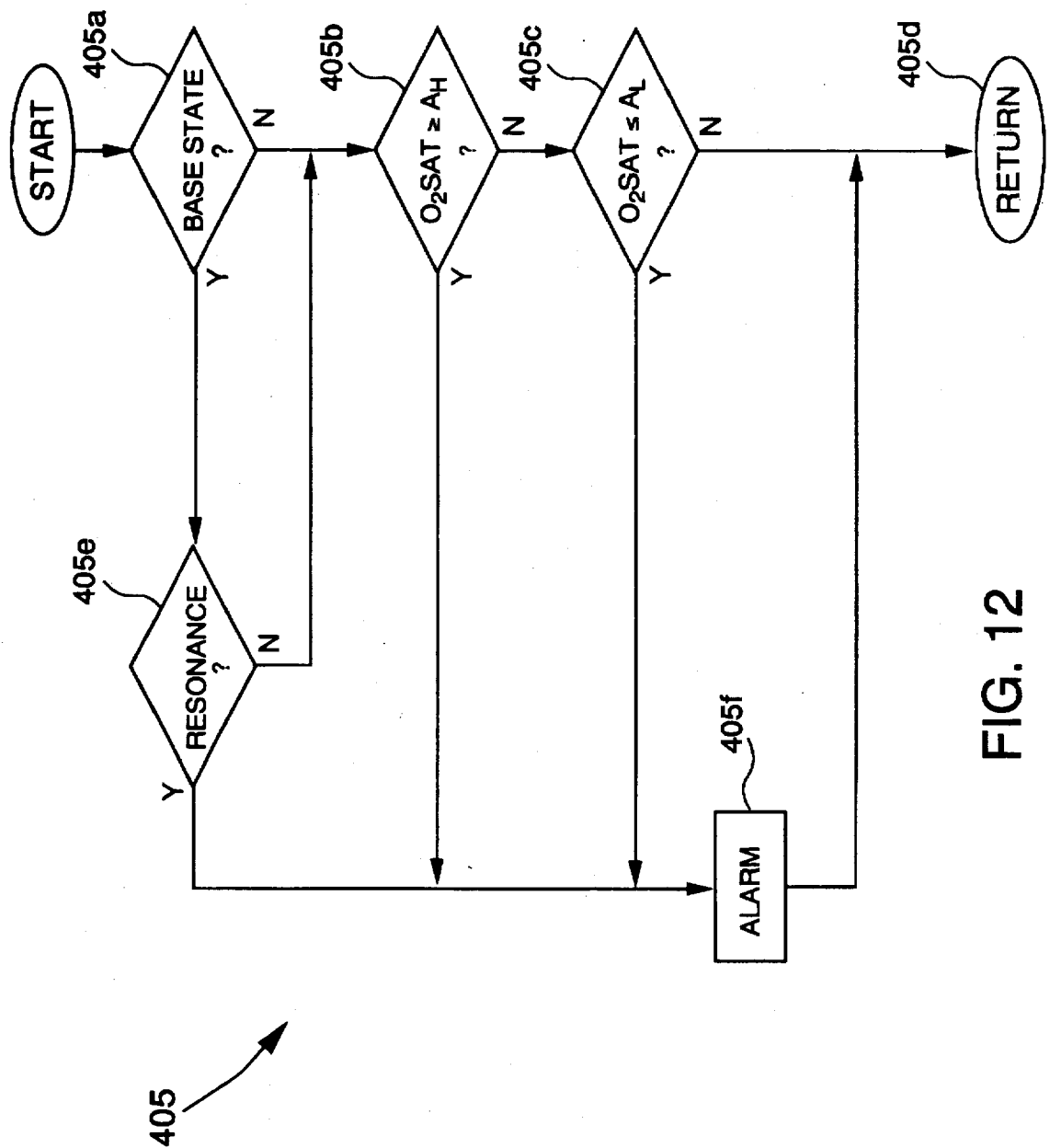
FIG. 12 is a flow chart illustrating the alarm mode utilized in all the embodiments of the present invention.

Still referring to FIG. 11a, at step 404, an initial dose rate is administered. The initial dose rate will be the maximum dose rate for the lowest range if $T_{O2}>O_2SAT$, i.e. for oxygenation; whereas, the initial dose rate will be the minimum dose rate for the lowest range if $T_{O2}<O_2SAT$, i.e. deoxygenation. The process continues with step 405 which determines if an alarm signal should be initiated. Step 405 is illustrated in FIG. 12 and discussed in greater detail below. Step 405 is executed after every subsequent step including steps 406 through 462 but is illustrated only once for the sake of clarity. Of course, an interrupt driven implementation of step 405, rather than a sequential implementation, may be most suitable for the present invention, as would be appreciated by one of ordinary skill in the art.

With continuing reference to FIG. 11a, at step 406, the current dose rate is maintained while pausing for $\tau_{CIRC}$ seconds. Step 406 is referred to as an adjustment state since it adjusts for the circulation delay of the subject. Preferably, a typical lung-foot circulation delay is about 5.1 seconds for a neonate. Although the duration of the adjustment states may be modified, typically only neonates clinically judged to have normal circulation times of about 5.1 seconds will qualify for device placement. Of course, a direct arm (or leg)-lung circulation time may be measured utilizing intravenous ether, as is well known. For this measurement, an olfactory correction of 0.4 seconds must be subtracted from the actual measured values. The actual value would then be used for the adjustment states durations.

Figure 13:
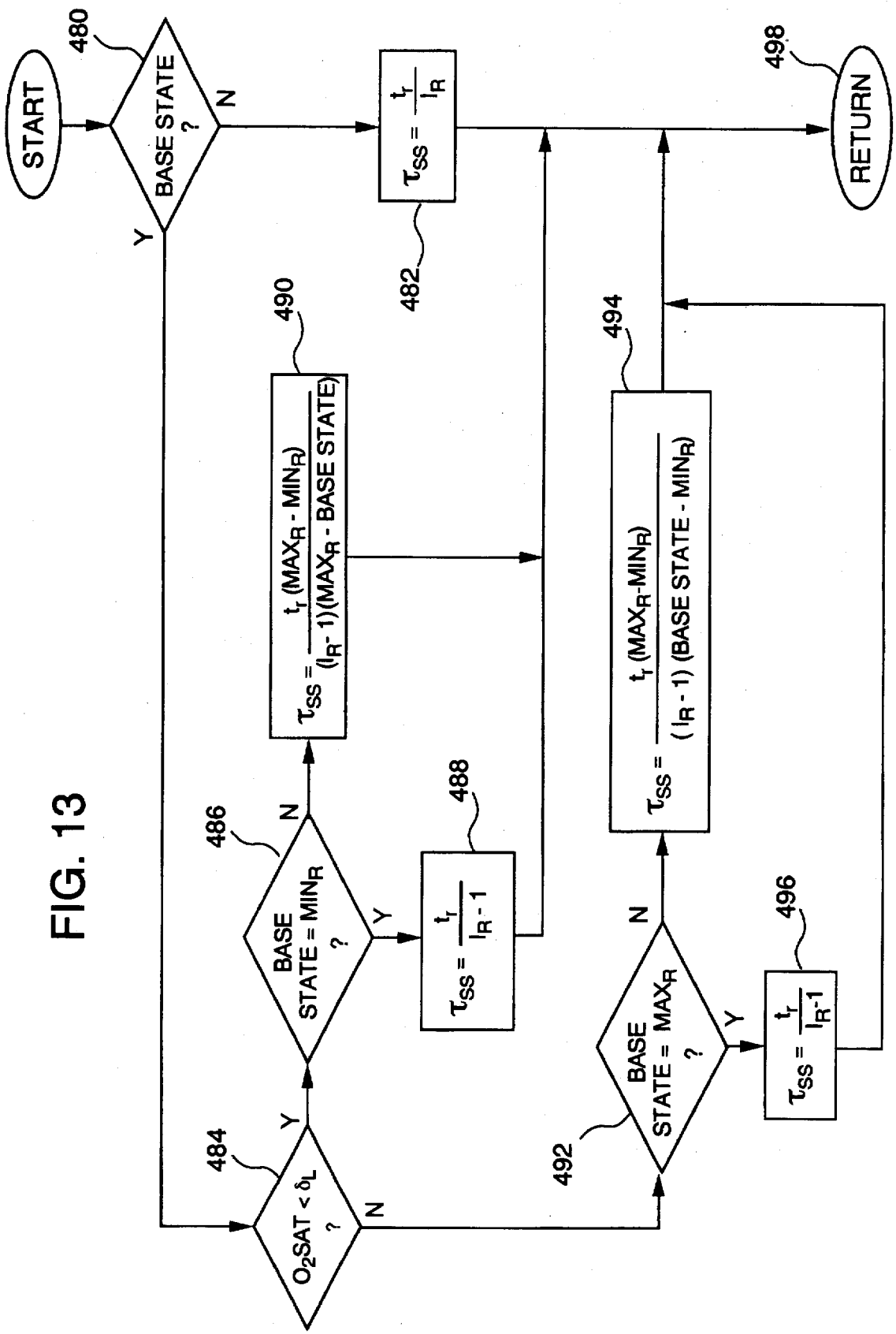
FIG. 13 is a flow chart illustrating the calculation of a series state delay time for use in all embodiments of the present invention.

As also shown in FIG. 11a, step 408 continues to deliver the current dose rate while pausing for $\tau_{ss}$ seconds. Step 408 is referred to as a series state and is necessary to coordinate the progression through the various possible dose rates with the time period determined by $t_r$. Preferably, $\tau_{ss}$ ranges from about 2.6 to about 42 seconds. The calculation for $\tau_{ss}$ depends on the current operating state. Some representative calculations are illustrated in FIG. 13 for a single-ranged implementation as discussed in greater detail below.

Still referring to FIG. 11a, at step 410 a test is performed to determine whether $O_2SAT$ is approaching $T_{O2}$. The actual test depends on whether $T_{O2}>O_2SAT$ or vice versa. In the former case (oxygenation), the condition is true if $O_2SAT$ is increasing, while in the latter case (deoxygenation), the condition is true if $O_2SAT$ is decreasing. If the condition at step 410 is true, processing continues with step 412. Otherwise, processing branches to step 426 (FIG. 11c). Step 412 maintains the current oxygen dose rate while again pausing for $\tau_{ss}$ seconds (as at step 408). At step 414, a test is performed to determine if the possible dose rate is the last possible dose rate in the current range. If other dose rates are available, the process continues with step 416 which progresses to the next possible dose rate. Thus, step 416 depends on whether $O_2SAT<T_{O2}$, or vice versa. If $O_2SAT<T_{O2}$, then the progression will be toward higher dose rates (increasing), whereas if $O_2SAT>T_{O2}$, then the progression will be toward lower dose rates (decreasing). If step 414 indicates that the possible dose rates in the current range have been exhausted, then processing continues with step 418 (FIG. 11b).

Figure 11B:
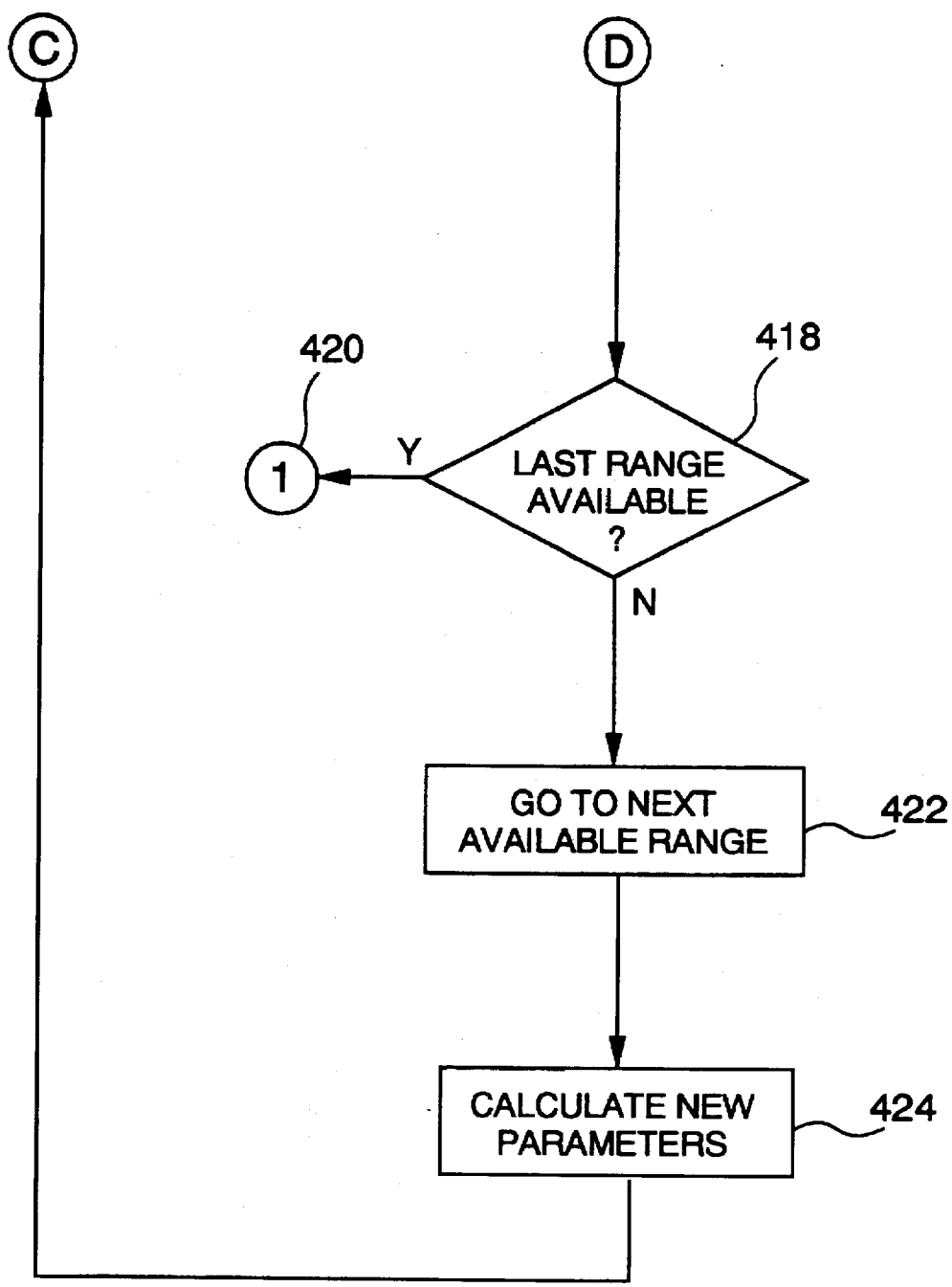
Figure 11C:
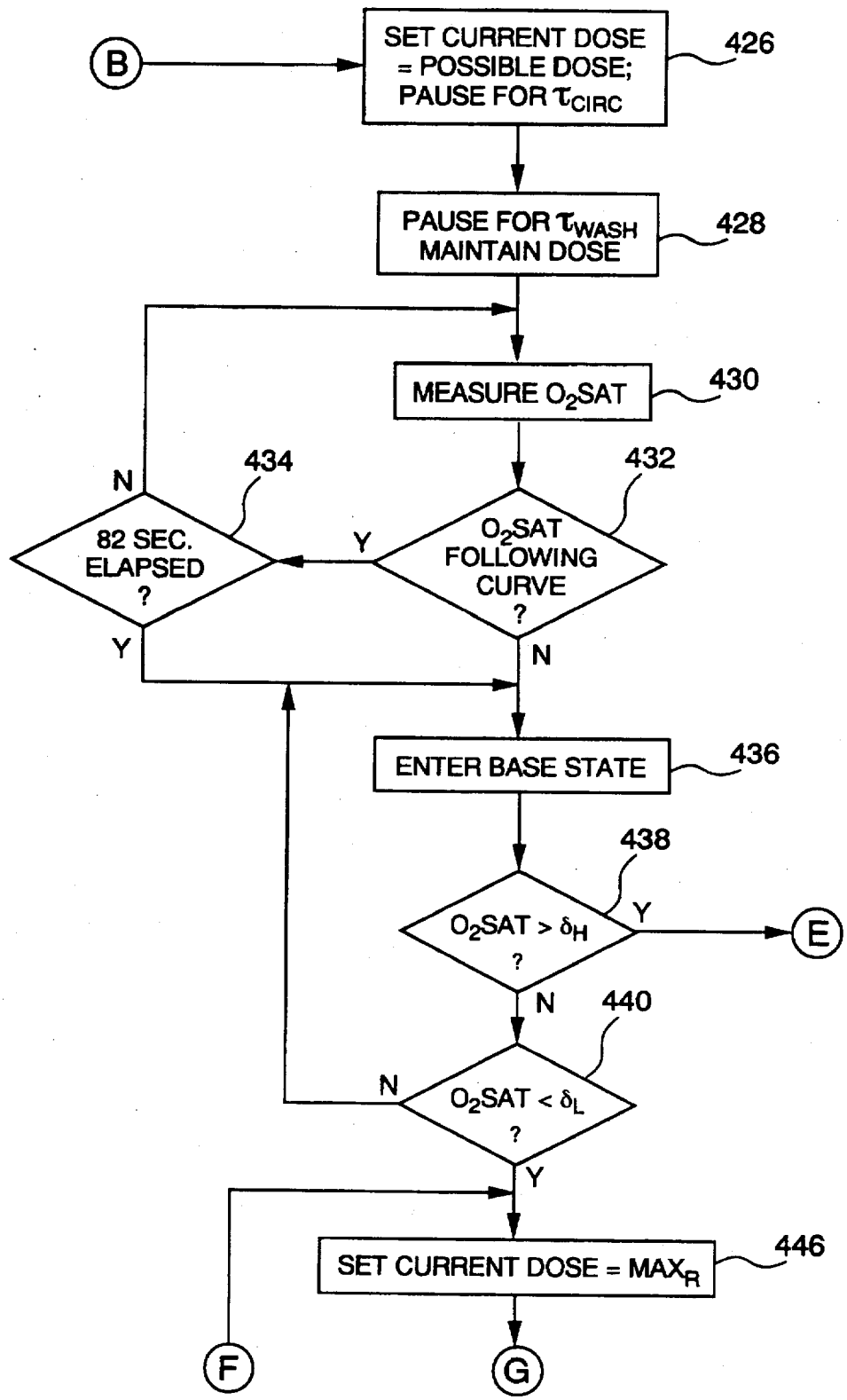

Referring now to FIG. 11b, at step 418 a test is performed to determine if the current range is the last available range. If the condition is false, then the possible dose rate is set to the dose rate in the next range which is closest to the previous possible dose rate. Thus, if the progression is increasing, the next possible dose rate will be the lowest in the next higher range. Whereas, if the progression is decreasing, the next possible dose rate will be the highest in the next lower range. If another range is not available, control branches to step 454 of FIG. 11d utilizing the maximum dose rate as illustrated by connector symbol 420. If step 418 determines another range is available, the next available range is entered at step 422. The appropriate corresponding parameters for the new range are calculated at step 424.

Processing also continues with step 426 of FIG. 11c if the condition tested at step 410 (FIG. 11a) is false, i.e. $O_2SAT$ has crossed $T_{O2}$ and is diverging therefrom. At step 426, the current possible dose rate becomes the current dose rate which is effected by the ECU. Step 426 also includes a pause for $\tau_{CIRC}$ to account for the circulation delay. At step 428, another pause for $\tau_{WASH}$ seconds is completed. Step 428 is referred to as a washout state which allows time for the physiological response to the new dose rate to stabilize. Preferably, $\tau_{WASH}$ is about 20 seconds. Step 430 is a measuring state which preferably lasts about 5 seconds. At step 432, a test is performed to determine if $O_2SAT$ is following the desired dose response curve which was stored in memory. If $O_2SAT$ is within some tolerance range (preferably±1% $O_2SAT$) of the desired curve, the condition is true. If true, processing continues with another test at step 434 which determines if a sufficient amount of time has elapsed such that $O_2SAT$ should be stable. Preferably, this time period will be approximately equal to $t_r$, or about 82 seconds.

With continuing reference to FIG. 11c, if the condition at step 434 is true, an appropriate base state is entered at step 436. Otherwise, the process returns to the measuring state at step 430. At step 438, a test is performed to determine if $O2SAT>\delta_H$. If the condition at step 438 is true, the current delivered dose is set to the minimum dose for the lowest range (Range 1) at step 442 of FIG. 11e. At step 444 of FIG. 11e, the possible dose progresses to the next lower dose since deoxygenation has been indicated. Control is then returned to step 450 of FIG. 11d.

Returning now to FIG. 11c, if the condition at step 438 is false, then another test is performed at step 440 to determine if $O_2SAT<\delta_L$. If the condition at step 440 is false, then the process returns to the previous base state at step 436. If the condition at step 440 is true, then the process continues at step 446 where the current dose is changed to the maximum dose for the current range ($max_R$).

Figure 11D:
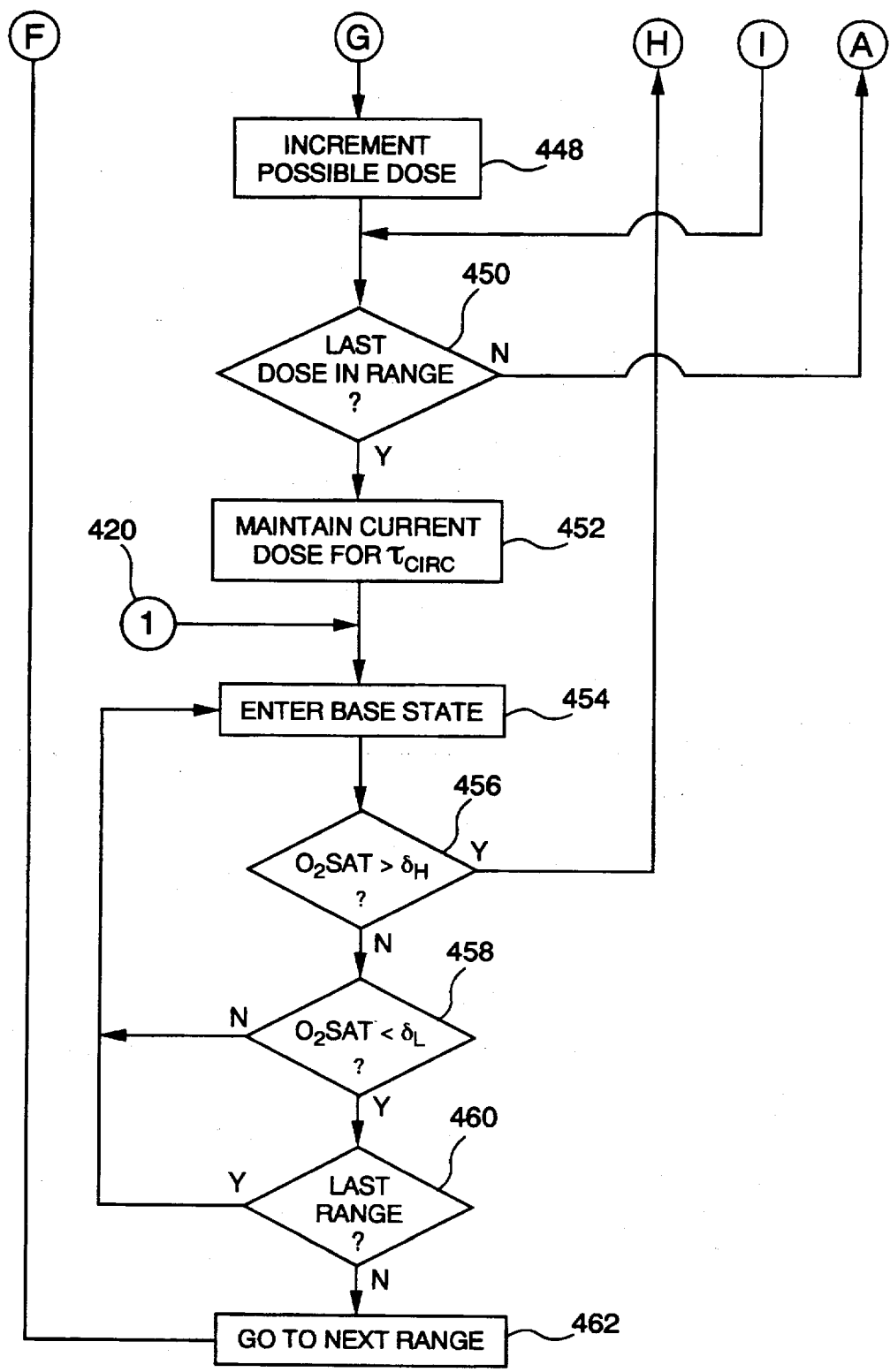
Figure 11E:
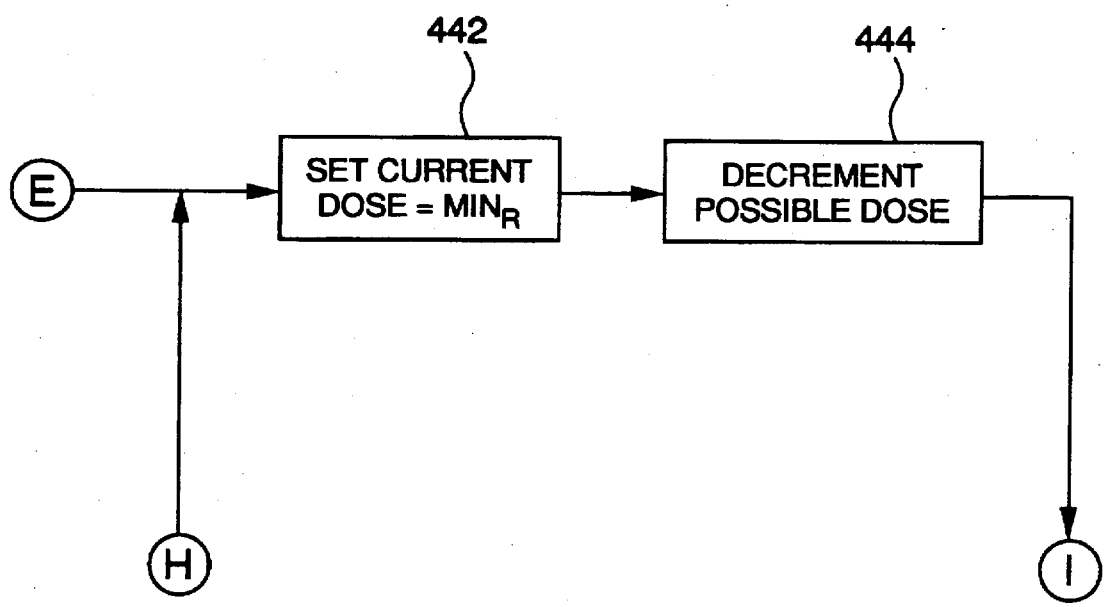

Referring now to FIG. 11d, the possible dose is incremented at step 448, since oxygenation has been indicated. At step 450, a test is performed, similar to the test of step 414, to determine if the current dose rate is the last (highest or lowest) in the current range. If the result of the test of step 450 is false, the process returns to step 406 (FIG. 11a, connector A). If the test of step 450 is true, step 452 continues to deliver the current dose (either $min_R$ or $max_R$) while pausing for $\tau_{CIRC}$ to account for the circulation delay. Step 454 again enters an appropriate base state which will correspond to either the minimum or maximum dose rate. Preferably, this base state, as well as the other base states, continues for about 5 seconds, although other durations could also be accommodated. Steps 456 and 458 test $O_2SAT$ similar to the tests of steps 438 and 440, respectively. Thus, if $O_2SAT>\delta_H$, the process is directed from step 456 back to step 442 (FIG. 11e, connector H). Similarly, if $O_2SAT<\delta_L$, the process is directed from step 458 back to the base state of step 454.

As also shown in FIG. 11d, step 460 determines if the current range is the last range available. If the condition of step 460 is true, the process returns to the base state of step 454. If the condition of step 460 is false, the process progresses to the next range at step 462 before returning to step 446 (FIG. 11c, Connector F). Step 462 selects an appropriate range depending upon whether the progression is increasing (oxygenation) or decreasing (deoxygenation).

Referring now to FIG. 12, a flow chart illustrating the alarm logic of step 405 in FIG. 11a is shown. The alarm mode logic is indicated generally by reference numeral 405 in FIG. 12. The alarm mode is utilized to alert the attending personnel to an abnormal condition. Such a condition may be the result of a machine malfunction or an adverse physiological response of the subject. The system activates an LED (light emitting diode) display to indicate the flow rate for the currently energized state. An LED display is also utilized to indicate the current blood oxygen saturation level and pulse rate as measured by the pulse oximeter. A machine malfunction may be ascertained after about 30 seconds of observation if the subject is hypoxic but a dose rate less than the highest dose rate is being delivered. Analogously, if a subject is hyperoxic and a dose rate greater than the minimum dose rate is being administered.

The alarm mode of FIG. 12 is used to detect extreme $O_2SAT$ levels or a resonant condition as discussed below. At step 405a, a test is performed to determine if the system is currently in a base state, since the resonance mode is defined as only occurring for base states. If not currently in a base state, processing continues with step 405b which performs a test to indicate if $O_2SAT \geq A_H$. Preferably, AH is set to about 96% for a neonate. If the result of step 405b is false, step 405c determines if $O_2SAT \leq A_L$, where $A_L$ is preferably about 89%. Of course, the values for $A_L$ and $A_H$ are adjusted appropriately depending upon the particular subject and the particular oxygenation strategy and equipment employed.

With continuing reference to FIG. 12, if the test of step 405c is false, control is returned to the flow chart of FIG. 11 by step 405d to the next subsequent step. For example, if control was passed to step 405 from step 408 of FIG. 11, step 405d of FIG. 12 would return control to step 410 of FIG. 11.

If the result of either step 405b or step 405c is true, an alarm is sounded by step 405f to alert attending personnel of an unusual condition. If the result of the test at step 405a is true, step 405e determines if the system is in a resonance mode.

Still referring to FIG. 12, to detect a resonance mode, the ECU tracks the occurrence of base state control possessions. Preferably, at least the last four (4) consecutive base states are stored in memory by the ECU. Resonance is indicated when system control alternates (oscillates) between two (2) nonadjacent base states for four (4) consecutive base state possessions. If resonance is detected, an alarm is sounded to enable attending personnel to switch the subject to standard oxygenation, or to effect other such appropriate action.

Although not the only cause of resonance, an inaccurate circulation delay time ($\tau_{CIRC}$) may result in a resonant mode. Thus, when resonance is detected, in addition to sounding an alarm, $\tau_{CIRC}$ may be modified in an attempt to eliminate the resonance. The circulation time may be adjusted manually, by attending personnel, or automatically, by the system. For example, if an abnormal circulation time is suspected, the actual circulation time may have to be measured via intravenous ether prior to device placement. The actual circulation time (less a 0.4 second olfactory correction) may be manually entered for $\tau_{CIRC}$ which is used in the adjustment states. Alternatively, the system may automatically modify (increment or decrement) the value for $\tau_{CIRC}$ by, preferably, 1 second intervals. Thus, a preferred embodiment has modes with adjustment states which vary from 5.5 seconds to 9.5 seconds at 1 second intervals.

Even if resonance is not present, a prolonged circulation time causes inaccurate oxygen dose selection. For example, if the circulation time delay utilized deviates from the actual value by 1 second, the system may select a nonoptimal base state. However, the base state selected will often be adjacent to the base state selected if an accurate circulation delay time were used. For the example above, the error in the delivered oxygen dose rate would then only be 0.03 L/min, 20% of the time. This error condition would be corrected in 30 seconds, but would add variance to the system. If the error in circulation time is closer to 2 seconds, the system may select a nonoptimal dose rate 40% of the time; whereas, if the error in the circulation delay time approaches 3 seconds, the system may select a nonoptimal dose rate 60% of the time. It is felt that neonates have circulation times within 3 seconds of the assumed value, so that they may be placed on the device without measuring actual circulation times.

Referring now to FIG. 13, a flow chart is shown illustrating representative calculations of $\tau_{ss}$ according to the present invention. One of these calculations, or an analagous calculation, is performed for each series state of FIGS. 11a through 11e such as those illustrated at steps 408 and 412. Returning now to FIG. 13, at step 480, a test is performed to determine if the system has reached a base state. If the result of the test at step 480 is false, then the series state delay is calculated by step 482 as:

$$\tau_{ss} = \frac{t_r}{T_R} \quad (1)$$

If the result of the test at step 480 is true, the process continues with step 484. At step 484, a test is performed to determine whether $O_2SAT<\delta_L$. If the result of the test at step 484 is true, then step 486 determines whether the most recent base state is the minimum base state for the current range. If the result of the test at step 486 is true, then the series state delay is calculated by step 488 as:

$$\tau_{ss} = \frac{t_r}{I_R - 1} \quad (2)$$

Step 498 then returns control to the series state which initiated the calculation.

With continuing reference to FIG. 13, if the result of the test at step 486 is false, then the series state delay is calculated by step 490 as:

$$\tau_{ss} = \frac{t_r * (\max_R - \min_R)}{(I_R - 1) * (\max_R - \text{base state})} \quad (3)$$

before control is returned to the series state via step 498. If the test performed at step 484 is false, then step 492 performs a test to determine if the most recent base state is the maximum base state for the current range. If the result of step 492 is true, then step 496 calculates the series state delay as:

$$\tau_{ss} = \frac{t_r}{I_R - 1} \quad (4)$$

Control is then returned to the appropriate series state via step 498. If the result of the test at step 492 is false, then the series state delay is calculated by step 494 as:

$$\tau_{ss} = \frac{t_r * (\max_R - \min_R)}{(I_R - 1) * (\text{base state} - \min_R)} \quad (5)$$

Step 498 then returns control to the appropriate series state. The calculations depicted in FIG. 13 are for a single range utilized for both oxygenation and deoxygenation. One of ordinary skill in the art should appreciate that the calculations may be modified to accommodate a number of possible permutations of ranges utilized for oxygenation and deoxygenation. For example, one range may be utilized for oxygenation while two ranges are utilized for deoxygenation.

A third embodiment of the present invention is closely related to the Neonatal Nasal Prong Oxydosimeter. The differences between the third (AFAO) embodiment and the Neonatal Nasal Prong Oxydosimeter embodiment are briefly summarized below.

The AFAO is a portable system and may be utilized to control oxygenation of adult patients. The AFAO may be used with patients having respiratory diseases including emphysema, restrictive lung disease, such as pulmonary fibrosis, congestive heart failure, acute bronchitis, asthma, and pneumonia, among others. The AFAO embodiment utilizes larger nasal prongs and its 33 increment, variably opening solenoid valve may be powered by a rechargeable battery or operate on standard household AC power. Furthermore, the AFAO embodiment uses a portable oxygen supply and an adult regulator-flowmeter set at a 5 L/min flow rate.

Operation of the AFAO embodiment is similar to the Neonatal Nasal Prong Oxydosimeter embodiment which was described in detail above and is illustrated in FIGS. 11a–11e, 12, and 13. Preferably, the AFAO uses oxygen dose rates ranging from about 0 L/min to about 5 L/min divided into two operating ranges. One additional consideration for use of the AFAO is that the system, as described, was designed for use with subjects having heart rates of at least 72 beats per minute corresponding to a shortest operating state of about 2.6 seconds. This is necessary so that the shortest operating state includes at least three (3) blood oxygen saturation level measurements. However, the system and method may be modified by increasing $t_r$, or by dividing the available doses into a series of ranges, to lengthen the shortest interval. This consideration was not discussed above since neonates typically have heart rates well above 72 beats per minute.

Preferably, an actual circulation time measurement is taken before device placement for the AFAO embodiment, since measurement of circulation times in adults is easier than measurement in neonates. Furthermore, adult circulation times are subject to greater variance than circulation times of neonates, such that it is more difficult to utilize an approximate value. As with the Neonatal Oxydosimeter, the system can modify the duration of adjustment states to account for variation in circulation times. For the AFAO embodiment, adjustment states may vary from about 5.5 seconds to about 14.5 seconds in 1 second increments.

Of course, system parameters, other than the circulation time delay, should be set appropriately for use in the AFAO embodiment. For example, the parameters which trigger the alarm mode (illustrated in FIG. 12) may be set such that $\delta_L$ equals 40% and $\delta_H$ is effectively ignored by setting it to a value which exceeds 100%. In this case, the extreme parameters for the alarm mode would function to inform the subject of a significant system fault, such as mispositioning of the pulse oximeter, or a low power condition.

The benefits to subjects or patients using the AFAO embodiment are similar to those described for the Neonatal Nasal Prong Oxydosimeter. Of course, use of the AFAO embodiment would not have the developmental effects of the Neonatal Nasal Prong Oxydosimeter. However, patients utilizing either system embodiment may develop better nitrogen balance since the systems simulate natural oxygenation better than previous systems. As a result, patients may feel more comfortable and be less likely to require advanced oxygenation. Furthermore, patients may be less likely to develop right-sided heart strain and failure. The effect of unrelated diseases, such as coronary artery disease, may be mollified as well resulting in patients living longer than previously expected. The AFAO may be suitable for use by a patient with COPD instead of the adult COPD oxydosimeter embodiment described above.

The AFAO may be adapted for use with a simple oxygen mask for patients who require more oxygen than can be supplied via the nasal prongs. Another application of the AFAO embodiment is for use by individuals requiring oxygen at high altitude. The operation of the system is unchanged, except for the regulator-flowmeter which is set to 10 L/min with flow rates spanning 5–10 L/min. System parameters may also be adjusted to exact optimal oxygenation under demanding circumstances. For example, for an individual at high altitudes, such as an aircraft pilot, $O_2SAT$ may be maintained at 98%. The device signals when it is no longer needed. The individual may then switch to the nasal prong embodiment as described above.

Depending on the particular application, different alarms may utilized to indicate various conditions. If a machine malfunction occurs, the individual could easily switch from automatic oxygenation controlled by the system to manual control of oxygenation.

Figure 14:
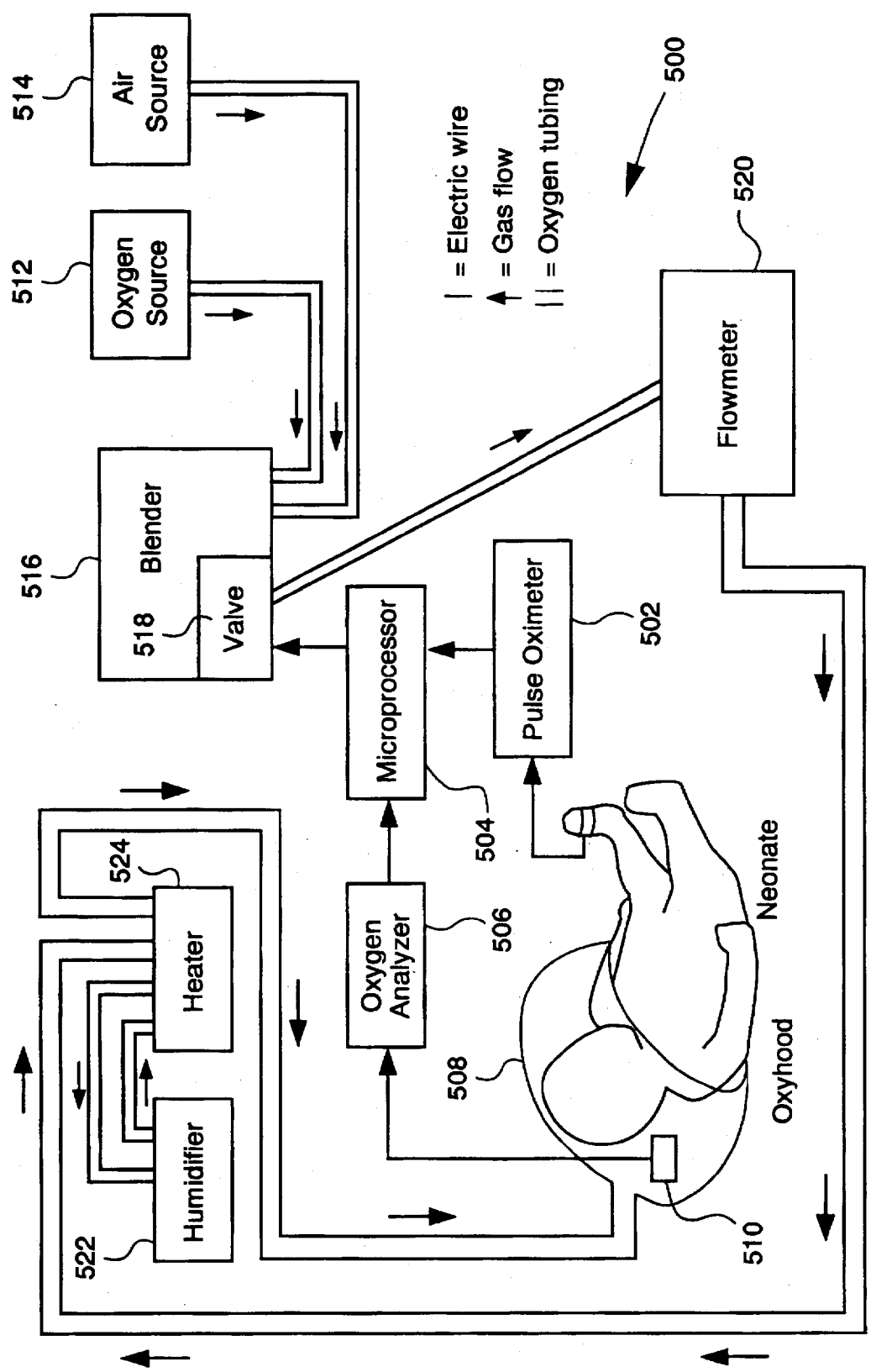
FIG. 14 is a block diagram illustrating another embodiment of the present invention for use as a Neonatal Oxyhood Oxydosimeter.

Referring now to FIG. 14, there is shown the fourth embodiment of the present invention, indicated generally by reference numeral 500, for use as a Neonatal Oxyhood Oxydosimeter. As illustrated, the oxydosimeter 500 includes a pulse oximeter 502 for attachment, preferably to the foot of the neonate. The pulse oximeter 502 supplies oxygen saturation data to a microprocessor 504. The microprocessor also receives data from an oxygen analyzer 506. The oxygen analyzer 506 receives data relating to the oxygen concentration within an oxyhood 508 from a probe 510 positioned within oxyhood 508, which preferably encloses the head of the neonate. The microprocessor also receives data and executes a control strategy to maintain oxygen saturation levels within a narrow predetermined range of acceptable values, based on the data from pulse oximeter 502 and oxygen analyzer 506, as described in greater detail below.

With continuing reference to FIG. 14, the Neonatal Oxyhood Oxydosimeter 500 also includes a pressurized oxygen source 512 and a pressurized air source 514, both of which are in fluid communication with a blender 516, such as the Model 3800 blender described above. The blender 516 preferably includes one or two valves, such as valve 518. Valve 518 is controlled by microprocessor 504 to dispense proper amounts of oxygen to the neonate. Preferably, microprocessor 504 controls blender 516 to deliver oxygen having a variable concentration, rather than controlling the flow rate as in the previous embodiments. In the illustrated embodiment, each valve, such as valve 518, is a 32-increment, variably opening, solenoid valve, such as that disclosed by the '773 patent referred to above. As shown, the valve (or valves) are in fluid communication with a flowmeter 520, such as the Model 0-3 described above. Flowmeter 520 is set to deliver about 9 L/min of oxygen through tubing to a humidifier 552 and then to an optional heater 524, prior to being delivered to the neonate. Oxygen concentration within oxyhood 508, preferably maintained between 22% and 60%, is preferably measured by an oxygen analyzer 506, such as the commercially available Model 473075 Mini Ox 3 oxygen monitor, manufactured by Catalyst Research in Owings Mills, Md.

The system and method for selecting a proper oxygen dose rate, as described above, works equally well for selecting a proper oxygen concentration. Instead of mapping oxygen flow rates across the physiological response curves of FIG. 10, the possible oxygen concentrations are utilized. For the Neonatal Oxyhood Oxydosimeter embodiment, 31 possible oxygen concentration states are used ranging from about 23.5% oxygen to 100% oxygen in 2.5% intervals. If the 100% oxygen concentration dose simulates the logarithmic function $y=\log_{1.6} x$ (curve A of FIG. 10), it will intersect the delta 2% line in about 0.76 seconds. This corresponds to a 23.5% oxygen concentration dose (or state). Curve G of FIG. 10 approximates the function $y=\log_9 x$ and intersects the delta 2% line at about 82 seconds, corresponding to a 100% oxygen concentration state. The remaining concentration doses are bounded by these doses.

Since all the states from 23.5% to 100% oxygen concentration are represented linearly with time on the x axis, and, since time and dosage are bounded, the system represents a dose selector. This is true even if the highest physiological response curve is below the delta 2% line at 82 seconds. In that case, the necessary dose to achieve the 2% increase in $O_2SAT$ must be higher than the highest available dose of the system. The system then utilizes the highest available dose and triggers an alarm if $O_2SAT$ is not within the predetermined limits.

Figure 15:
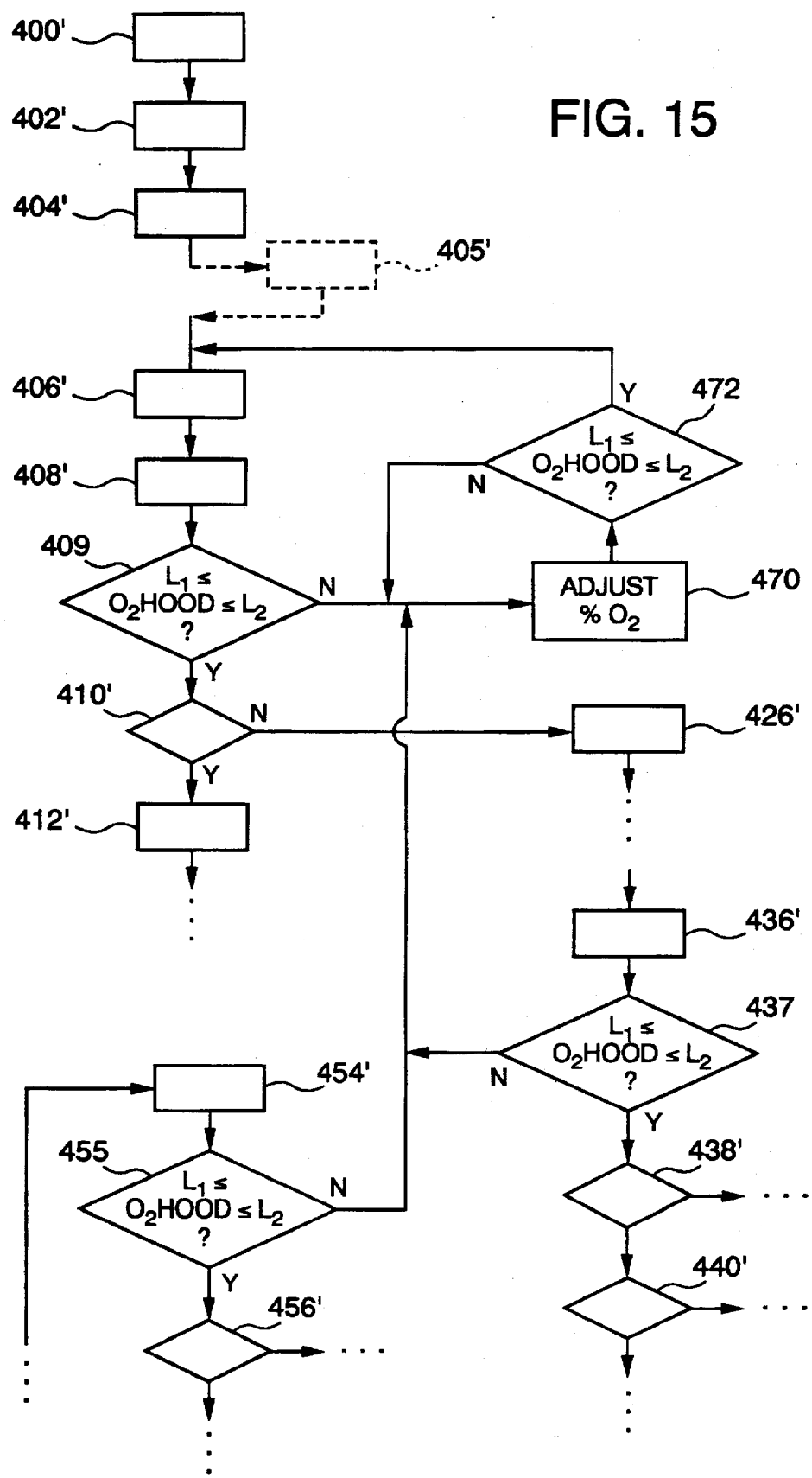
FIG. 15 is a partial flow chart illustrating the operation of the system of FIG. 14 and its similarity to the operation illustrated in FIGS. 11a–11e.

Referring now to FIG. 15, a partial flow chart is shown illustrating the operation of the Neonatal Oxyhood Oxydosimeter embodiment. Since this embodiment operates in a manner similar to the Neonatal Nasal Prong Oxydosimeter and the AFAO, that discussion is incorporated by reference here. The steps identified by primed reference numerals, i.e. 400', operate analogously to the steps identified by unprimed reference numerals of FIGS. 11a–11e. The necessary modifications to the flow charts of FIGS. 11a–11e are discussed below.

As shown in FIG. 15, an additional test is performed at step 409 to determine if the oxygen concentration under the oxyhood ($O_2HOOD$) is within the predetermined limits ($L_1$ and $L_2$). Preferably, $O_2HOOD$ is determined by oxygen analyzer 506 of FIG. 14. Also preferably, $L_1$ is about 22% oxygen concentration and $L_2$ is about 60% oxygen concentration. If the result of the test at step 409 is true, the process continues with step 410' as discussed for FIG. 11a. If the result of the test at step 409 is false, control is passed to step 470 to adjust the $O_2$ concentration. Step 470 attempts to bring the oxygen concentration under the oxyhood within the predetermined limits. Thus, if $O_2HOOD>L_2$, then step 470 adjusts blender 516 to provide compressed air having an oxygen concentration of about 21%. Whereas, if $O2HOOD<L1$, then step 470 adjusts blender 516 to provide oxygen at about 100% concentration.

Still referring to FIG. 15, $O_2HOOD$ is monitored at step 472 while the adjusted oxygen concentration is delivered to oxyhood 508. Control loops back to step 470 until $O_2HOOD$ is within the limits determined by $L_1$ and $L_2$, then control returns to step 406'. Thus, unlike the previous embodiments, step 470 interrupts the timing progression toward $t_r$ so that the process must be restarted. Similarly, step 437 is inserted between step 436' and step 438', and step 455 is inserted between steps 454' and 456', to monitor $O_2HOOD$. For either step 437 or step 455, if $O_2HOOD$ is outside of the predetermined limits, control is directed to step 470 to adjust the delivered $O_2$ concentration.

As with the embodiments already discussed, the embodiment for use as a Neonatal Oxyhood Oxydosimeter includes a mode for automatically adjusting the circulation time delay. An alarm mode is also included to detect unusual O2SAT measurements due to adverse physiological response in the patient, or due to machine malfunction. This embodiment, as well as the various other embodiments has the ability to maintain blood oxygen saturation levels within a narrow range of values, or at a specific value within the range of measurement error, by appropriate selection of the system parameters.

Figure 16:
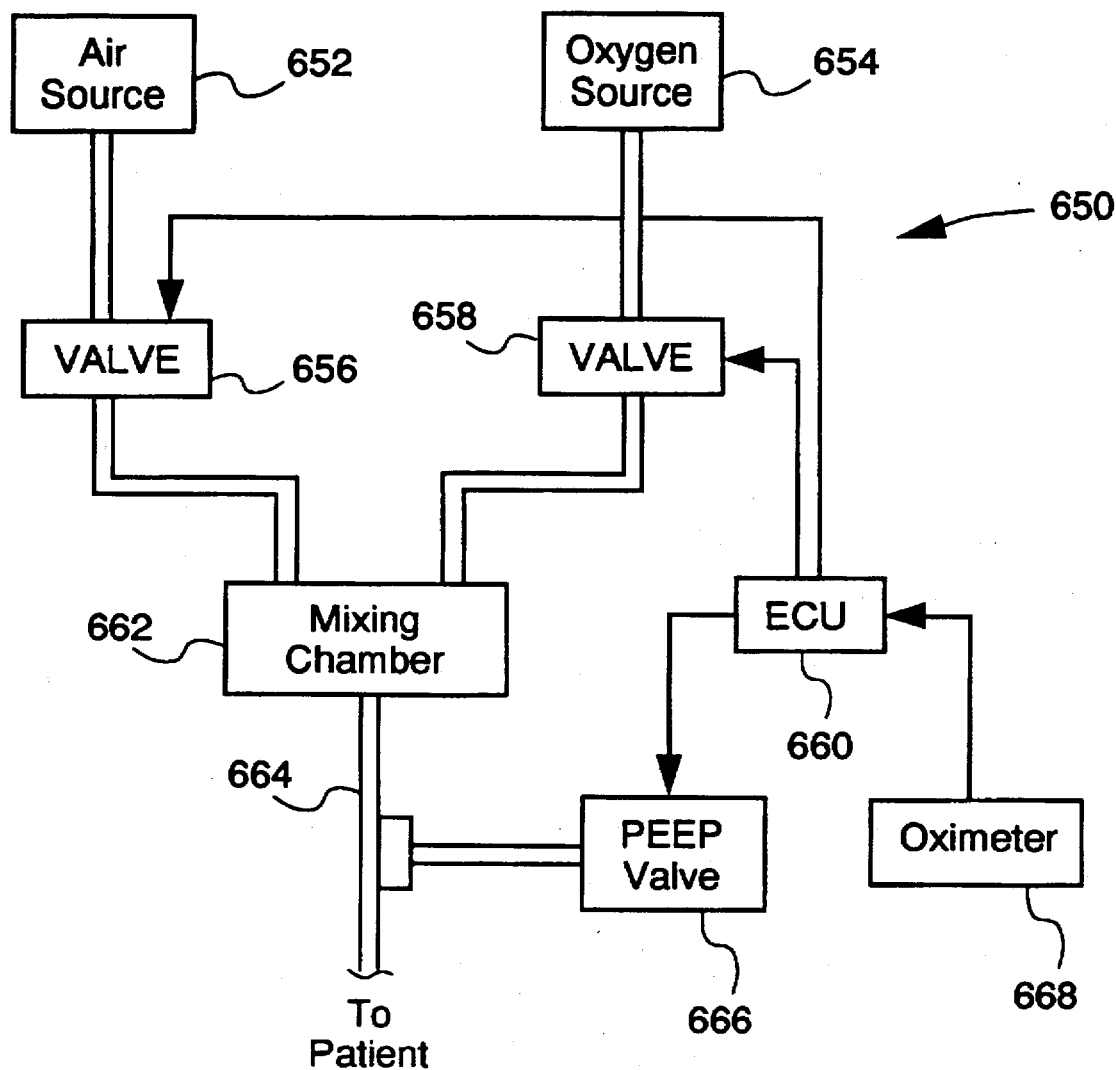
FIG. 16 is a block diagram illustrating an embodiment of the present invention for use as an Adult Respirator.

Referring now to FIG. 16, a fifth embodiment of the present invention, indicated generally by reference numeral 650, is shown. As illustrated, the fifth embodiment 650 includes a pressurized air source 652 and a pressurized oxygen source 654, both of which are in fluid communication with two complementary mixer valves 656 and 658, respectively. Valves 656 and 658 are variably opening, 31 increment solenoid valves with a coulomb controlling circuit, controlled by the ECU 660 according to the control strategy of the present invention. The oximeter 668 measures blood oxygen saturation levels and delivers representative signals to ECU 660. By controlling valves 656 and 658, varying amounts of air and oxygen are provided to a mixing chamber 662. Oxygen at varying concentrations is then output from mixing chamber 662 and, after compression, communicated to the patient via tubing 664. This oxygen may be introduced to the patient utilizing an endotracheal tube, a nasal-tracheal tube, a tracheostomy tube, or the like.

As also illustrated in FIG. 16, oxydosimeter 650 also includes a positive end expiratory pressure (PEEP) valve 666 controlled by ECU 660. PEEP valve 666 is a simple, on/off solenoid valve, unlike the variably opening complementary valves 656 and 658. The complementary mixer valves 656 and 658 and the PEEP valve 666 are controlled by ECU 660 based on data from pulse oximeter 668. PEEP valve 666 may be intermittently controlled to provide an additional amount of pressurized oxygen to the patient as the patient exhales (expires) air from the lungs. In a preferred embodiment, constant use of PEEP is utilized to preserve the continuity of the available doses. Generally, the ECU controls complementary mixer valves 656 and 658 and PEEP valve 666 to deliver oxygen at varying concentrations so as to maintain a desired blood oxygen saturation level in the patient.

The selection of a proper oxygen dose follows the flow charts of FIGS. 11a–11e with oxygen concentrations substituted for flow rates. Thus, the minimum dose corresponds to 23.5% $O_2$ concentration while the maximum dose corresponds to 100% $O_2$ concentration. If desirable, a number of dosage ranges may be used. For example, a first range spanning 23.5% to 60% O2 concentration, and a second range spanning 62.5% to 100% concentration, may be used. As with the AFAO, to accommodate heart rates below 72 beats per minute, a number of dose ranges may be used, or $t_r$ may be increased, to assure at least three (3) heart beats during the shortest operating state.

Figure 17:
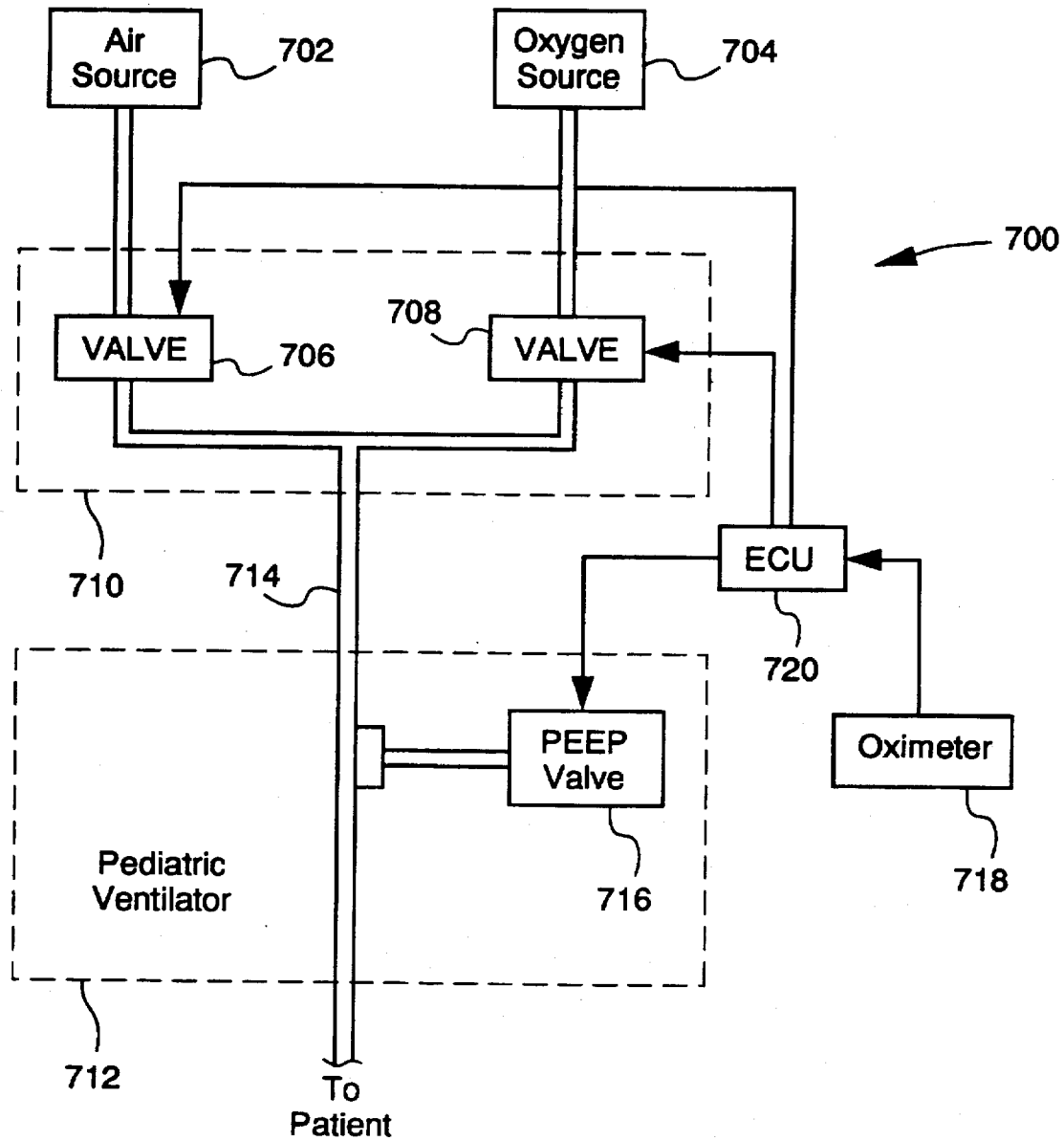
FIG. 17 is a block diagram illustrating an embodiment of the present invention for use as a Neonatal Respirator.

Referring now to FIG. 17, a sixth embodiment of the present invention is shown. The sixth embodiment is particularly suited for use as a Neonatal Respirator, indicated generally by reference numeral 700. The sixth embodiment functions similar to the fifth embodiment, illustrated in FIG. 16. Thus, it includes a pressurized air source 702, and a pressurized oxygen source 704. However, the gases are compressed to a lesser degree. Unlike the fifth embodiment, however, valves 706 and 708 are disposed within blender 710. Furthermore, valves 706 and 708 are directly connected to free standing pediatric ventilator 712 via tubing 714. Thus, a mixing chamber is not utilized. Each valve 712, 714 has 31 increments in the illustrated embodiment. PEEP valve 716 delivers pressurized gases constantly, as in the adult embodiment, for the same reasons discussed there. Oximeter 718 is connected to a foot of a neonate to measure $O_2SAT$ and communicate representative signals to ECU 720. Nasal-tracheal tubes are generally not used for the Neonatal Respirator. Otherwise, both devices are identical. Thus, the proper dose selection follows the flow charts of FIGS. 11a–11e utilizing oxygen concentrations in place of flow rates.

The administration of CPAP (continuous positive airway pressure) is a well known technique used to oxygenate neonates immediately before or after ventilator placement. The seventh embodiment of the present invention may be appreciated by referring again to FIG. 17. The CPAP device differs from the Neonatal Respirator in that PEEP is not used. Furthermore, a neonate is connected to the pediatric ventilator by oxygen tubing and a nasal canula, firmly attached to the neonate's nares. The ventilator functions in CPAP mode.

Since the operation of this embodiment is virtually identical to the general method for proper oxygen dosage selection discussed in the description of the Neonatal Nasal Prong Oxydosimeter, that discussion is incorporated by reference here. Again, instead of selecting flow rates, oxygen concentrations are selected ranging from about 23.5% $O_2$ to near 100% $O_2$.

Combination Modes

Minor modifications may provide combinations of operating modes, which were utilized in the various embodiments described above, to provide other embodiments having greater versatility and effectiveness. For example, the fifth embodiment and the third embodiment may be modified to accommodate pulse rates below 72, but responsiveness is decreased due to the doubling of the intervals. To improve the responsiveness, an additional test condition may be inserted immediately after the first test state and after every base state. The condition would monitor the pulse rate to determine whether the pulse rate is less than 72 beats per minute. If the inserted test condition were true, control would be directed to a corresponding state having a shortest time interval equal to 5.2 seconds. If false, control would be directed to a corresponding state having a shortest time interval equal to 2.6 seconds. Thus, three (3) beats per shortest time interval is assured in all cases, while also optimizing system responsiveness. Similar combination modes may be used with high altitude applications of the third embodiment, in which simple oxygen masks having a 5–10 L/min flow rate are used, as described above.

It is understood, of course, that while the forms of the invention herein shown and described include the best mode contemplated for carrying out the invention, they are not intended to illustrate all possible forms thereof. It will also be understood that the words used are descriptive rather than limiting, and that various changes may be made without departing from the spirit and scope of the invention disclosed.

What is claimed is:

1. A method for maintaining a desired blood oxygen saturation level within a first predetermined range of values having an upper limit and a lower limit so as to reduce variation of the blood oxygen saturation level, the method being adapted for use with an oxydosimeter including an electronic control unit (ECU) having memory, a pulse oximeter attached to a patient for measuring a current blood oxygen saturation level of the patient, and an oxygen delivery system controlled by the ECU for delivering a selected oxygen dose to the patient, the oxygen delivery system having a plurality of sequential oxygen doses ranging from a first oxygen dose to a second oxygen dose, the method comprising:

delivering the second oxygen dose to the patient while repeatedly sequencing through the plurality of sequential oxygen doses beginning with the first oxygen dose and proceeding to an adjacent oxygen dose in the sequence after a predetermined time interval has elapsed until the current blood oxygen saturation level of the patient attains the desired blood oxygen saturation level at which point a corresponding oxygen dose is selected from the plurality of sequential oxygen doses;

delivering the selected oxygen dose to the patient so as to maintain the desired blood oxygen saturation level; and energizing an alarm when a predetermined number of oscillations between any two nonadjacent oxygen doses is detected.

2. The method of claim 1 wherein the current blood oxygen saturation level is determined by:

storing a sequence of blood oxygen saturation values in the memory, the sequence containing at least three measurement values obtained from the pulse oximeter;

determining the median value of the at least three measurements; and calculating a mean value using the sequence values which are within a predetermined range of the median value, the predetermined range depending upon characteristics of the oxydosimeter, the mean value representing the current blood oxygen saturation level.

3. The method of claim 1 wherein the current blood oxygen saturation level is determined by:

storing a sequence of blood oxygen saturation values in the memory, the sequence containing at least three measurement values obtained from the pulse oximeter;

determining the median value of the at least three measurement values; and selecting the most recently stored value, which is within a predetermined range of the median value, from the sequence of values, the predetermined range depending upon characteristics of the oxydosimeter, the most recently stored value representing the current blood oxygen saturation level.

4. The method of claim 1 wherein the plurality of sequential oxygen doses comprises a plurality of discrete oxygen flow rates.

5. The method of claim 1 wherein the plurality of sequential oxygen doses comprises a plurality of discrete oxygen concentrations.

6. A system for maintaining a desired blood oxygen saturation level within a first predetermined range of values having an upper limit and a lower limit so as to reduce variation of the blood oxygen saturation level, the system including an electronic control unit (ECU) having memory, a pulse oximeter attached to a patient for measuring a current blood oxygen saturation level of the patient, and oxygen delivery apparatus controlled by the ECU for delivering a selected oxygen dose to the patient, the oxygen delivery apparatus having a plurality of sequential oxygen doses ranging from a first oxygen dose to a second oxygen dose, the system comprising:

means for delivering the second oxygen dose to the patient while repeatedly sequencing through the plurality of sequential oxygen doses beginning with the first oxygen dose and proceeding to an adjacent oxygen dose in the sequence after a predetermined time interval has elapsed until the current blood oxygen saturation level of the patient attains the desired blood oxygen saturation level at which point a corresponding oxygen dose is selected from the plurality of sequential oxygen doses;

means for delivering the selected oxygen dose to the patient so as to maintain the desired blood oxygen saturation level; and an alarm for indicating when a predetermined number of oscillations between any two nonadjacent oxygen doses is detected.

7. The system of claim 6 wherein the current blood oxygen saturation level is determined by:

means for storing a sequence of blood oxygen saturation values in the memory, the sequence containing at least three measurement values obtained from the pulse oximeter;

means for determining the median value of the at least three measurements; and means for calculating a mean value using the sequence values which are within a predetermined range of the median value, the predetermined range depending upon characteristics of the oxydosimeter, the mean value representing the current blood oxygen saturation level.

8. The system of claim 6 wherein the current blood oxygen saturation level is determined by:

means for storing a sequence of blood oxygen saturation values in the memory, the sequence containing at least three measurement values obtained from the pulse oximeter;

means for determining the median value of the at least three measurement values; and means for selecting the most recently stored value, which is within a predetermined range of the median value, from the sequence of values, the predetermined range depending upon characteristics of the oxydosimeter, the most recently stored value representing the current blood oxygen saturation level.

9. The system of claim 6 wherein the plurality of sequential oxygen doses comprises a plurality of discrete oxygen flow rates.

10. The system of claim 6 wherein the plurality of sequential oxygen doses comprises a plurality of discrete oxygen concentrations.

11. A method for maintaining a desired blood oxygen saturation level within a first predetermined range of values having an upper limit and a lower limit so as to reduce variation of the blood oxygen saturation level, the method being adapted for use with an oxydosimeter including an electronic control unit (ECU) having memory, a pulse oximeter attached to a patient for measuring a current blood oxygen saturation level of the patient, and an oxygen delivery system controlled by the ECU for delivering a selected oxygen dose to the patient, the oxygen delivery system having a plurality of sequential oxygen doses ranging from a first oxygen dose to a second oxygen dose, the method comprising:

delivering the second oxygen dose to the patient while sequencing through the plurality of sequential oxygen doses beginning with the first oxygen dose and proceeding to an adjacent oxygen dose in the sequence after a predetermined time interval has elapsed until the current blood oxygen saturation level of the patient attains the desired blood oxygen saturation level, at which point a corresponding oxygen dose is selected from the plurality of sequential oxygen doses; and delivering the selected oxygen dose to the patient so as to maintain the desired blood oxygen saturation level, wherein the predetermined time interval is based on circulation time of the patient, the predetermined time interval being adjusted when a predetermined number of oscillations between any two nonadjacent oxygen doses is detected.

12. The method of claim 11 wherein the predetermined time interval is adjusted by about one second.

* * * * *